United States Patent
Gregerson et al.

(10) Patent No.: US 7,490,982 B2
(45) Date of Patent: *Feb. 17, 2009

(54) GANTRY POSITIONING APPARATUS FOR X-RAY IMAGING

(75) Inventors: Eugene A. Gregerson, Bolton, MA (US); Richard K. Grant, Sudbury, MA (US); Norbert J. Johnson, North Andover, MA (US)

(73) Assignee: Medtronic Navigation, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/262,299

(22) Filed: Oct. 27, 2005

(65) Prior Publication Data

US 2006/0120511 A1 Jun. 8, 2006

Related U.S. Application Data

(63) Continuation of application No. 10/645,322, filed on Aug. 21, 2003, now Pat. No. 7,338,207.

(60) Provisional application No. 60/405,098, filed on Aug. 21, 2002.

(51) Int. Cl.
*H05G 1/02* (2006.01)
(52) U.S. Cl. .................................. 378/197; 378/193
(58) Field of Classification Search .............. 378/15, 378/193, 196–198, 189
See application file for complete search history.

(56) References Cited

U.S. PATENT DOCUMENTS 3,549,885 A 12/1970 Andersson (Continued)

FOREIGN PATENT DOCUMENTS

CN 1 032 188 C 7/1996

(Continued)

OTHER PUBLICATIONS

Chabbal, J., et al., "Amorphous Silicon X-Ray Image Sensor", *Physics of Medical Imaging*, Proceedings of SPIE, Feb. 23-25, 1997, vol. 3032.

(Continued)

*Primary Examiner*—Hoon Song
(74) *Attorney, Agent, or Firm*—Hamilton, Brook, Smith & Reynolds, P.C.

(57) ABSTRACT

A robotically controlled five degree-of-freedom x-ray gantry positioning apparatus, which is connected to a mobile cart, ceiling, floor, wall, or patient table, is being disclosed. The positioning system can be attached to a cantilevered o-shaped or c-shaped gantry. The positioning system can precisely translate the attached gantry in the three orthogonal axes X-Y-Z and orient the gantry about the X-axis and Y-axis while keeping the center of the gantry fixed, (see FIG. 1). The positioning apparatus provides both iso-centric and non iso-centric "Tilt" and "Wag" rotations of the gantry around the X-axis and Y-axis respectively. The iso-centric "Wag" rotation is a multi-axis combination of two translations and one rotation. Additionally, a field of view larger than that provided by the detector is provided in pure AP (anterior/posterior) and lateral detector positions through additional combinations of multi-axis coordinated motion. Each axis can be manually controlled or motorized with position feedback to allow storage of gantry transformations. Motorized axes enable the gantry to quickly and accurately return to preset gantry positions and orientations. A system and method for enlarging the field of view of the object being imaged combines a rotation of the x-ray source and detector with a multi-axis translation of the gantry.

14 Claims, 21 Drawing Sheets

FIG. 1

U.S. PATENT DOCUMENTS

| | | | |
|---|---|---|---|
| 3,617,749 | A | 11/1971 | Massiot |
| 4,200,799 | A | 4/1980 | Saito |
| 4,352,986 | A | 10/1982 | Pfeiler |
| 4,442,489 | A | 4/1984 | Wagner |
| 4,481,656 | A | 11/1984 | Janssen et al. |
| 4,741,015 | A | 4/1988 | Charrier |
| 4,803,714 | A | 2/1989 | Vlasbloem |
| 4,810,881 | A | 3/1989 | Berger et al. |
| 4,829,252 | A | 5/1989 | Kaufman |
| 4,875,228 | A | 10/1989 | Archer |
| 4,884,293 | A | 11/1989 | Koyama |
| 4,935,949 | A | 6/1990 | Fujita et al. |
| 4,955,046 | A | 9/1990 | Siczek et al. |
| 4,982,415 | A | 1/1991 | Shibata et al. |
| 4,987,585 | A | 1/1991 | Kidd et al. |
| 5,014,292 | A | 5/1991 | Siczek et al. |
| 5,014,293 | A * | 5/1991 | Boyd et al. .................. 378/197 |
| 5,032,990 | A | 7/1991 | Eberhard et al. |
| D323,386 | S | 1/1992 | Perusek |
| 5,084,908 | A | 1/1992 | Alberici et al. |
| 5,095,501 | A | 3/1992 | Kobayashi |
| 5,097,497 | A | 3/1992 | Deucher et al. |
| 5,159,622 | A | 10/1992 | Sakaniwa et al. |
| 5,187,659 | A | 2/1993 | Eberhard et al. |
| 5,265,610 | A | 11/1993 | Darrow et al. |
| 5,287,274 | A | 2/1994 | Saint Felix et al. |
| D345,606 | S | 3/1994 | Perusek |
| 5,319,693 | A | 6/1994 | Eberhard et al. |
| 5,390,112 | A | 2/1995 | Tam |
| 5,448,607 | A | 9/1995 | McKenna |
| 5,448,608 | A | 9/1995 | Swain et al. |
| 5,452,337 | A | 9/1995 | Endo et al. |
| 5,499,415 | A | 3/1996 | McKenna |
| 5,515,416 | A | 5/1996 | Siczek et al. |
| 5,583,909 | A | 12/1996 | Hanover |
| 5,592,523 | A | 1/1997 | Tuy et al. |
| 5,598,453 | A | 1/1997 | Baba et al. |
| 5,625,660 | A | 4/1997 | Tuy |
| 5,638,419 | A | 6/1997 | Ingwersen |
| 5,661,772 | A | 8/1997 | Bär et al. |
| 5,668,846 | A | 9/1997 | Fox et al. |
| 5,740,222 | A | 4/1998 | Fujita et al. |
| 5,740,224 | A | 4/1998 | Müller et al. |
| 5,745,545 | A | 4/1998 | Hughes |
| 5,784,428 | A | 7/1998 | Schmidt |
| 5,802,138 | A | 9/1998 | Glasser et al. |
| 5,912,943 | A | 6/1999 | Deucher et al. |
| RE36,415 | E | 11/1999 | McKenna |
| 6,041,097 | A | 3/2000 | Roos et al. |
| 6,113,264 | A | 9/2000 | Watanabe |
| 6,130,930 | A | 10/2000 | Tam |
| 6,147,352 | A | 11/2000 | Ashburn |
| 6,203,196 | B1 | 3/2001 | Meyer et al. |
| 6,212,251 | B1 | 4/2001 | Tomura et al. |
| 6,215,841 | B1 * | 4/2001 | Hsieh ............................ 378/8 |
| 6,289,073 | B1 | 9/2001 | Sasaki et al. |
| 6,314,157 | B1 | 11/2001 | Tachizaki |
| 6,322,251 | B1 | 11/2001 | Ballhaus et al. |
| 6,324,246 | B1 | 11/2001 | Ruimi |
| 6,325,537 | B1 | 12/2001 | Watanabe |
| 6,435,715 | B1 | 8/2002 | Betz et al. |
| 6,442,235 | B2 | 8/2002 | Koppe et al. |
| 6,484,049 | B1 | 11/2002 | Seeley et al. |
| 6,487,267 | B1 | 11/2002 | Wolter |
| 6,496,558 | B2 | 12/2002 | Graumann |
| 6,519,312 | B1 | 2/2003 | Tybinowski et al. |
| 6,546,068 | B1 | 4/2003 | Shimura |
| 6,582,120 | B2 | 6/2003 | Schomberg |
| 6,590,953 | B2 | 7/2003 | Suzuki et al. |
| 6,609,826 | B1 * | 8/2003 | Fujii et al. .................. 378/198 |
| 6,614,871 | B1 | 9/2003 | Kobiki et al. |
| 6,619,840 | B2 | 9/2003 | Rasche et al. |
| 6,742,929 | B2 | 6/2004 | Horbaschek |
| 6,869,217 | B2 | 3/2005 | Rasche et al. |
| 6,940,941 | B2 | 9/2005 | Gregerson et al. |
| 6,990,170 | B2 | 1/2006 | Sugihara et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,338,207 | B2 * | 3/2008 | Gregerson et al. .......... 378/198 |
| 2001/0005410 | A1 | 6/2001 | Rasche et al. |
| 2002/0118793 | A1 | 8/2002 | Horbaschek |
| 2002/0168053 | A1 | 11/2002 | Schomberg |
| 2003/0072416 | A1 | 4/2003 | Rasche et al. |
| 2004/0170254 | A1 | 9/2004 | Gregerson et al. |
| 2007/0086566 | A1 | 4/2007 | Gregerson et al. |
| 2007/0104308 | A1 | 5/2007 | Gregerson et al. |

FOREIGN PATENT DOCUMENTS

| | | |
|---|---|---|
| DE | 89 05 588.8 | 9/1990 |
| DE | 195 35 583 A1 | 3/1997 |
| DE | 198 39 825 C1 | 7/1999 |
| DE | 199 27 953 A1 | 1/2001 |
| EP | 0 231 969 | 1/1987 |
| EP | 0 471 455 A2 | 2/1992 |
| EP | 0 564 292 A2 | 10/1992 |
| EP | 0 564 292 | 10/1993 |
| EP | 0 810 005 A2 | 12/1997 |
| EP | 1 090 585 A1 | 4/2001 |
| FR | 2 304 321 | 10/1976 |
| GB | 2 088 670 A | 6/1982 |
| JP | 2000-312674 A | 11/2000 |
| WO | WO 96/06561 | 3/1996 |

OTHER PUBLICATIONS

Hsiung, H., et al., "3D x-ray angiography: Study of factors affecting projection data consistency", *Physics of Medical Imaging*, Proceedings of SPIE, pp. 226-237, Feb. 23-25, 1997, vol. 3032.

Lwata, K., et al., "Description of a Prototype Combined CT-SPECT System with a Single CdZnTE Detector", *Nuclear Science Symposium Conference Record*, 2000 IEEE, XP010556613, pp. 16-1-16-5.

Lang, T.F., et al., "A Prototype Emission-Transmission Imaging System", *Proceedings of the Nuclear Science Symposium and Medical Imaging Conference*, 1991 IEEE, XP010058199, pp. 1902-1906.

Lang, Thomas, F., et al., "Description of a Prototype Emission—Transmission Computed Tomography Imaging System", *Journal of Nuclear Medicine, Society of Nuclear Medicine*, 1992, XP002901050, pp. 1881-1887.

Hein, et al., "Double-Centering Method for Increasing Efficiency of Cone-Beam X-Ray CT Reconstruction," IEEE, pp. 1728, 2002.

* cited by examiner

FIG. 6A    FIG. 6B    FIG. 6C
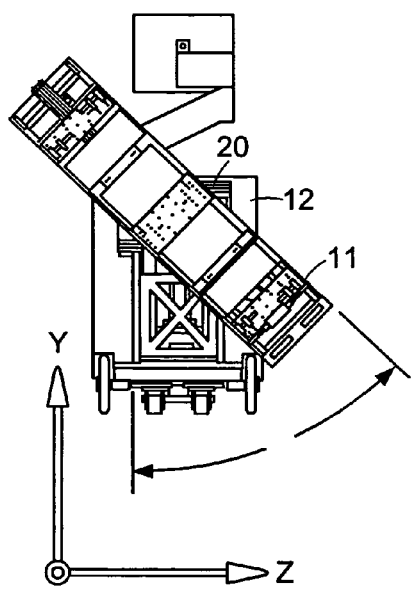 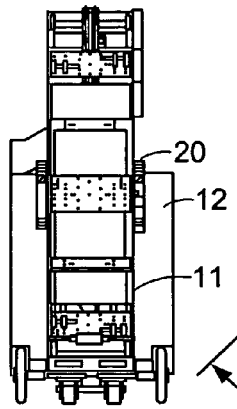 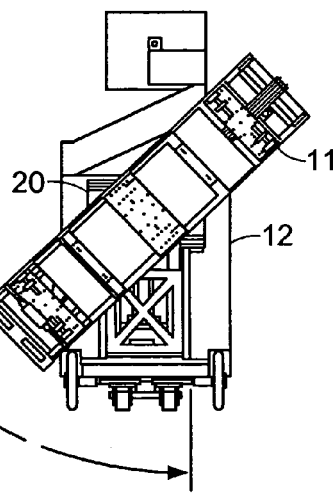
FIG. 7A    FIG. 7B    FIG. 7C
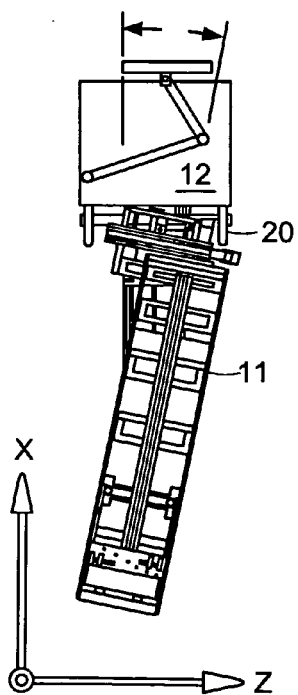 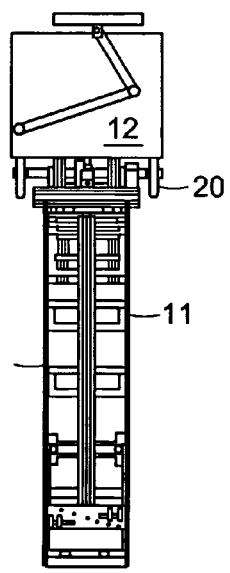 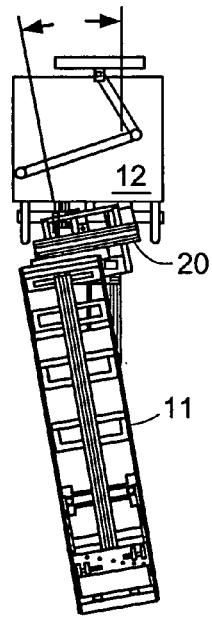

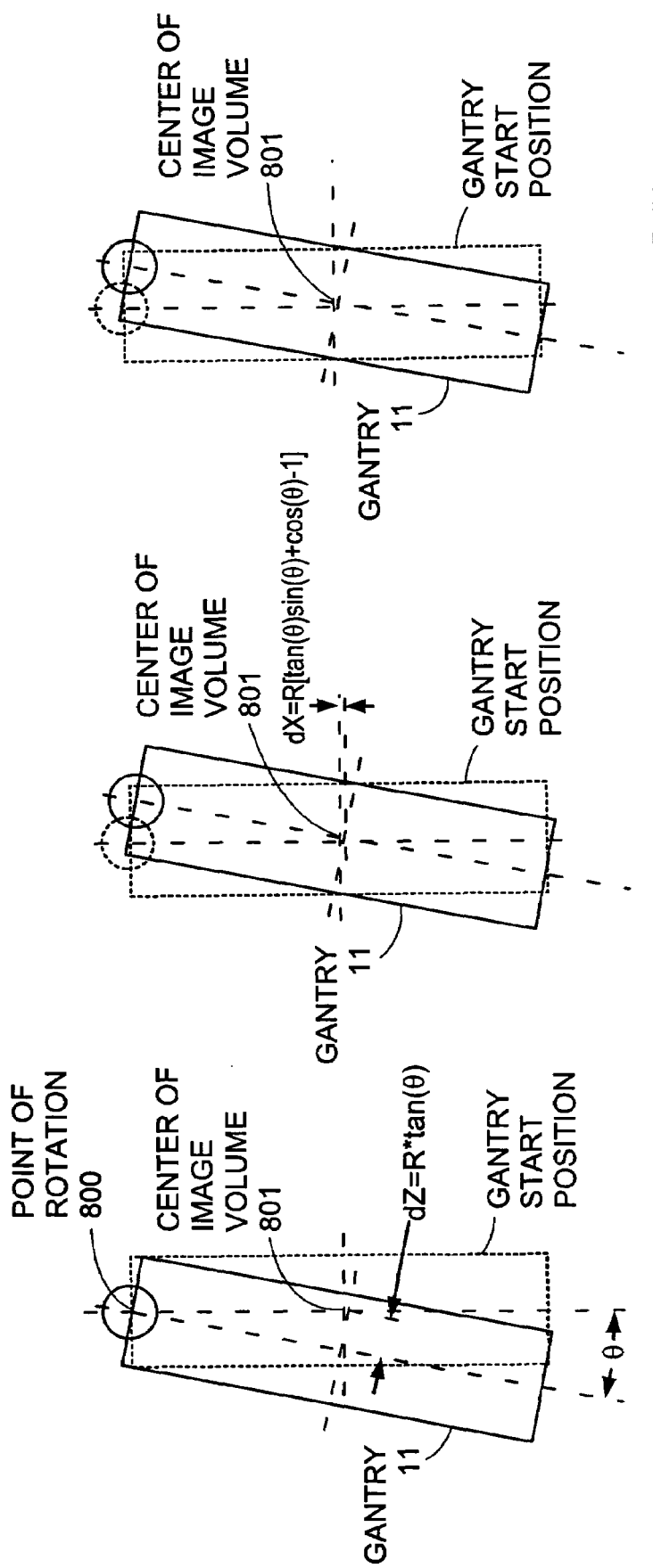

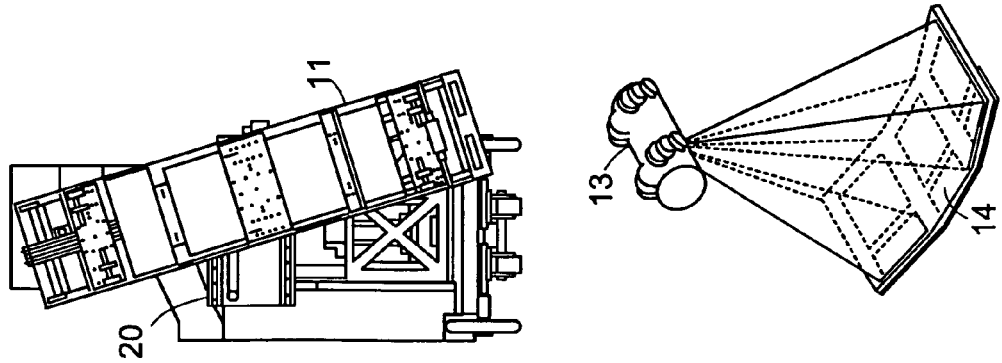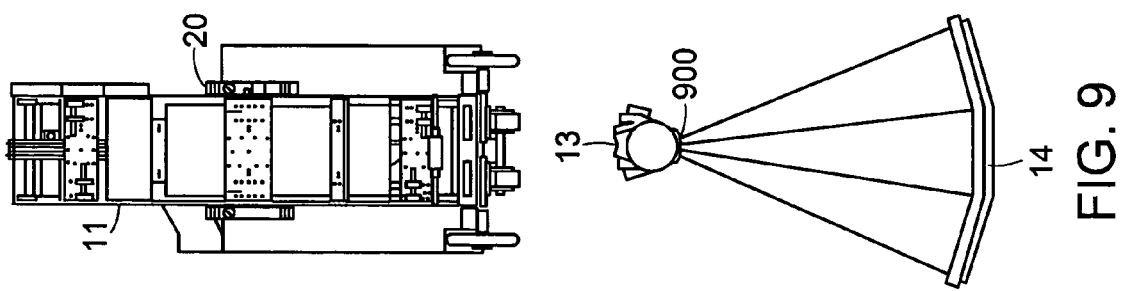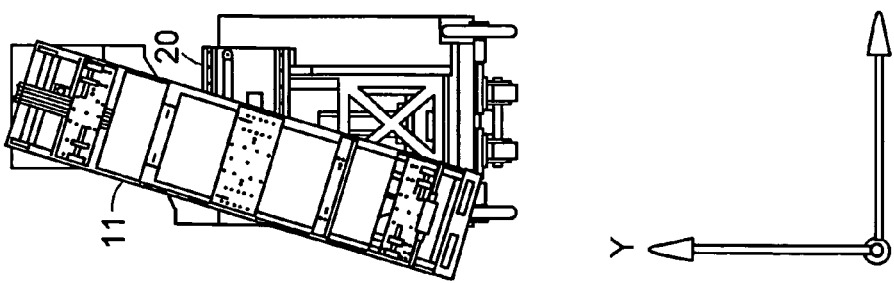
FIG. 9

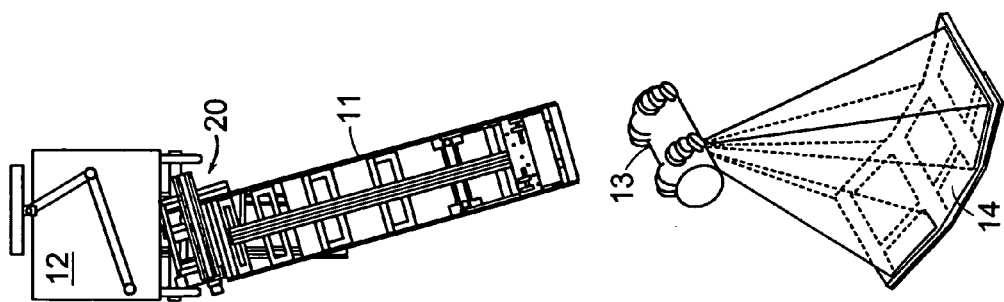
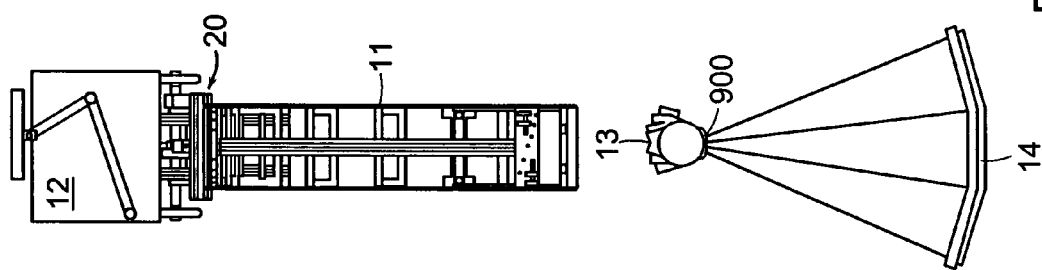
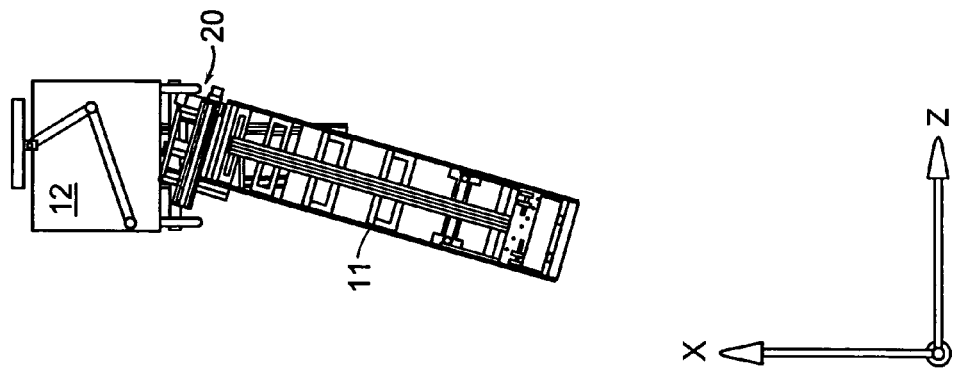
FIG. 10

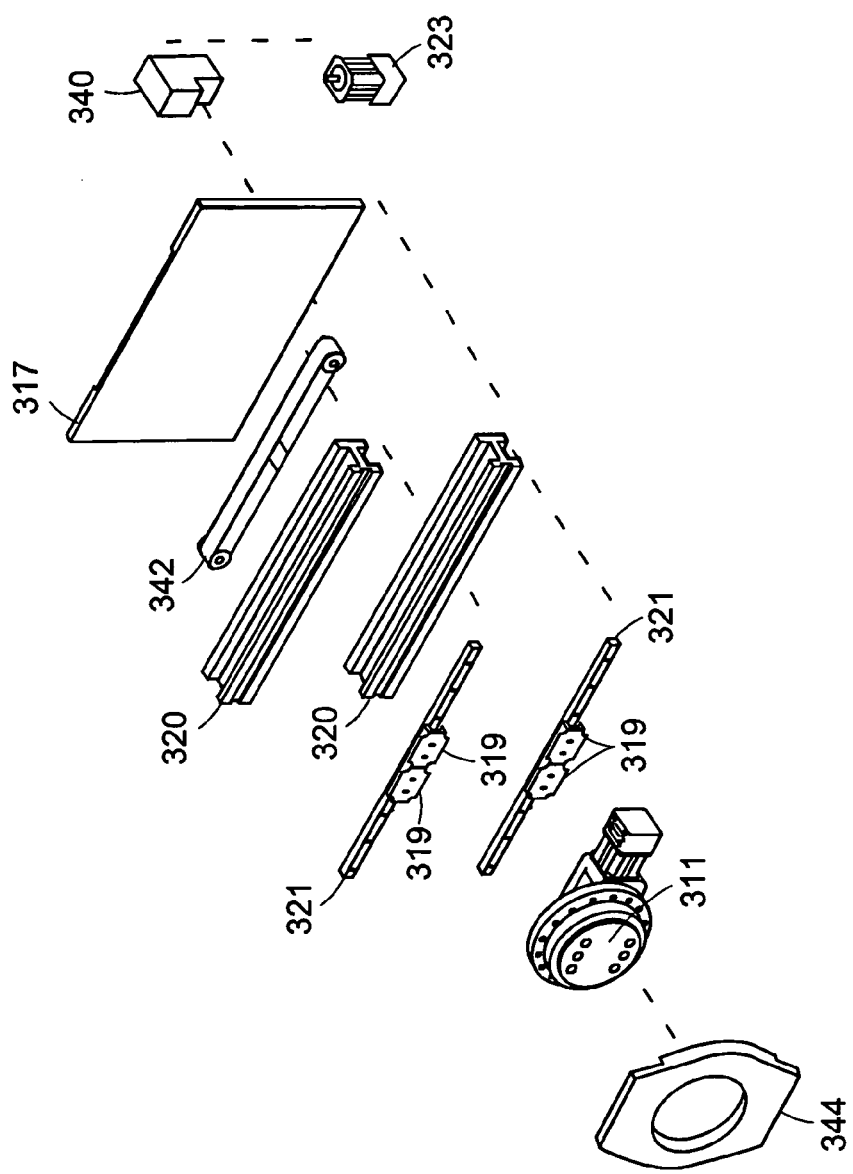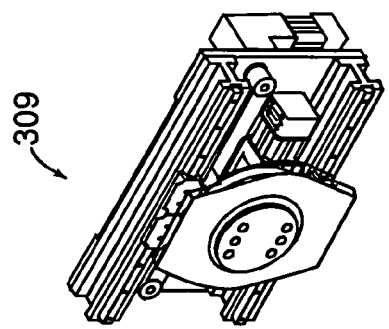
FIG. 15

GANTRY POSITIONING APPARATUS FOR X-RAY IMAGING

RELATED APPLICATIONS

This application is a continuation of U.S. application Ser. No. 10/645,322, filed Aug. 21, 2003 now U.S. Pat. No. 7,337,207, which claims the benefit of U.S. Provisional Application No. 60/405,098, filed Aug. 21, 2002, the entire teachings of which are incorporated herein by reference. U.S. application Ser. No. 10/645,322, filed Aug. 21, 2003 is related to U.S. application Ser. No. 10/459,405, filed on Jun. 11, 2003, the entire teachings of which are incorporated herein by reference.

BACKGROUND OF THE INVENTION

Healthcare practices have shown the tremendous value of three-dimensional imaging, mainly as a diagnostic tool in the Radiology Department. Other areas of care, including the operating room, intensive care departments and emergency departments, rely on two-dimensional imaging (fluoroscopy, ultrasound, 2-D mobile X-ray) as the primary means of diagnosis and therapeutic guidance. This is mainly due to the cost, size, and expertise required to operate traditional three-dimensional devices. Moreover, radiologic quality CT scanners have been designed to maximize image quality at the expense of mobility. Truly practical and mobile imaging solutions for "non-radiology departments" capable of performing both 2D and 3D imaging in the same device have yet to be developed. Previous attempts simply do not address the true need, which is to maintain a sizable volume while meeting a level of expected image quality. In the past, there have been two types of devices proposed to address this need. One type of device uses a mobile C-arm and spins it around the anatomy, such as the SIREMOBIL ISO-C$^{3D}$ imaging system from Siemens AG. These C-arm based attempts have a limited field of view, are procedurally cumbersome and have an inherent limit to the image quality.

Others have attempted to make a fixed-bore CT mobile, such as the device described in Butler W. E. et al, A Mobile CT Scanner with Intraoperative and ICU Application, 1998. (http://neurosurgery.mgh.harvard.edu/mobileCT.htm). However, these so-called "mobile CT scanners" are characterized by the elevated dosing level of a traditional fixed CT scanner, they are difficult to maneuver, and they are incapable of performing 2D imaging when that is all that is needed.

In general, the fluoroscopic C-arm attempts meet the criteria of mobility and flexibility, but fall short on image quality and image volume. The "mobile CT scanner" attempts meet the criteria of image volume and quality, but fail to address the practical issues of usability and cost. Additionally, state of the art CT scanners are incapable of translating and tilting in the same fashion of mobile fluoroscopy systems.

A truly mobile and practical solution for 'non-radiology department' 3-D imaging also capable of performing 2D imaging does not yet exist. This is mainly due to the fact that current tomographic scanners are not mobile in a practical manner. The inability to move a CT scanner with the same degrees of freedom of mobile C-arrns has hindered the acceptance and use of mobile three-dimensional imaging. This has limited the value of three-dimensional computed tomographic imaging to areas mainly as a diagnostic tool in the Radiology Department.

There is a need for a mobile CT scanner for use in the operating room, intensive care unit, emergency room and other parts of the hospital, in ambulatory surgery centers, physician offices, and the military battlefield, which is truly mobile, can translate and tilt in multiple degrees-of-freedom, and is capable of performing both 2D and 3D x-ray imaging.

SUMMARY OF THE INVENTION

The present invention relates in one aspect to a method and apparatus for positioning a gantry of a radiation imaging system with respect to an object to be imaged. In one embodiment, a positioning apparatus provides up to five degrees-of-freedom for the gantry, including translational movement along three orthogonal axes (X-Y-Z), and rotational movement around the X- and Y-axes.

A five degree-of-freedom gantry positioning apparatus for a radiation imaging system comprises a first linear positioner for translating a gantry in a first direction relative to the support structure; a second linear positioner for translating the gantry in a second direction relative to the support structure, the second direction being orthogonal to the first direction; a third linear positioner for translating the gantry in a third direction relative to the support structure, the third direction being orthogonal to the first and second directions; a first rotary positioner for rotating the gantry about a first axis relative to the support structure; and a second rotary positioner for rotating the gantry about a second axis relative to the support structure. A control system actuates the positioning apparatus to move the gantry to pre-defined positions an orientations. The pre-defined positions and orientations can be set by a user, or can be set based upon stored positioning data. Preferably, the positioning apparatus includes a position feedback mechanism for determining the location and/or orientation of the gantry in three-dimensional space.

The gantry positioning apparatus can be connected one end to a support structure, such as a mobile cart, ceiling, floor, wall, or patient table, and can be attached on the other end to a gantry, such as an O-shaped or C-shaped gantry, to support the gantry in a cantilevered fashion. The gantry positioning apparatus can position the gantry manually, or can be motorized with position feedback to allow storage of particular gantry positions and orientations. The positioning apparatus is particularly advantageous for medical imaging applications, including 3D computerized tomographic (CT) imaging and 2D x-ray radiographic scanning, as well as other medical, scientific, and industrial applications.

In another aspect, a gantry positioning apparatus provides both iso-centric and non iso-centric "tilt" and "wag" rotations of the gantry around the X-axis and Y-axis respectively. The iso-centric "wag," or y-axis, rotation accomplished by a combination of translational and rotational motions of the gantry positioning apparatus.

More generally, an imaging system of the invention comprises a gantry having a radiation source and a detector operable to obtain images of an object positioned inside the gantry; a support structure; and a gantry positioning apparatus that secures the gantry to the support structure in a cantilevered manner. The positioning apparatus is operable to rotate the gantry about a first axis that is parallel to, and non-collinear with, an iso-centric axis of the gantry. As used herein, an iso-centric axis of the gantry is an axis tjat intersects the center of the gantry image volume (i.e. the iso-center), such as the vertical axis of the gantry. A control system actuates the gantry positioning apparatus to rotate the gantry about the first axis, and to translate the gantry in second and third axes, so as to approximate a rotation of the gantry about the iso-centric axis of the gantry.

The invention further relates to a method of rotating a gantry about an iso-centric axis, comprising rotating the gantry about an axis that is parallel to and non-collinear with an iso-centric axis; translating the gantry a first distance in a first direction; and translating the gantry a second distance in a second direction so as to maintain the iso-center of the gantry in a fixed position.

In yet another aspect, the present invention relates to systems and methods for increasing the field-of-view in a radiation imaging system. In one embodiment, a relatively large field-of-view is obtained by simulating a rotation of the gantry assembly about the focal spot of the radiation source when the source and detector are in a pure anterior/posterior or pure lateral positions. Rotations about the focal spot are possible through a multi-axis combination of one rotation and two translations. By moving the gantry assembly to two or three gantry positions rotated about the focal spot, and digitally "stitching" together the resultant data a large field-of-view image is acquired.

In still another aspect, the invention relates to gantry imaging systems and methods for enlarging the field of view of an object being imaged which combine a rotation of a radiation source and detector within a gantry with a multi-axis translation of the gantry. The gantry is translated to move the detector closer to the object being imaged, thus increasing the field-of-view. Preferably, the detector is moved tangent to a "virtual circle" within the gantry that is centered on and contains the object to be imaged. As the source and detector rotate through the gantry, the gantry translates in coordination, so that the detector remains tangent to the virtual circle, similar to the motion of a "hula hoop" on the torso of a person.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6A-6C shows a gantry positioning apparatus rotating the gantry ring about the x-axis;

FIGS. 7A-7C shows a gantry positioning apparatus rotating the gantry ring about the y-axis;

FIGS. 8A-8C illustrates a method of performing iso-centric "wag" rotation about the y-axis;

FIG. 9 illustrates a method of titling a gantry about the focal spot of the x-ray source to obtain a large field-of-view anterior-posterior x-ray image;

FIG. 10 illustrates a method of tilting a gantry about the focal spot of the x-ray source to obtain a large field-of-view lateral x-ray image;

FIG. 15 shows the positioning apparatus for z-axis translation;

DETAILED DESCRIPTION OF THE INVENTION

A description of preferred embodiments of the invention follows.

Figure 1:
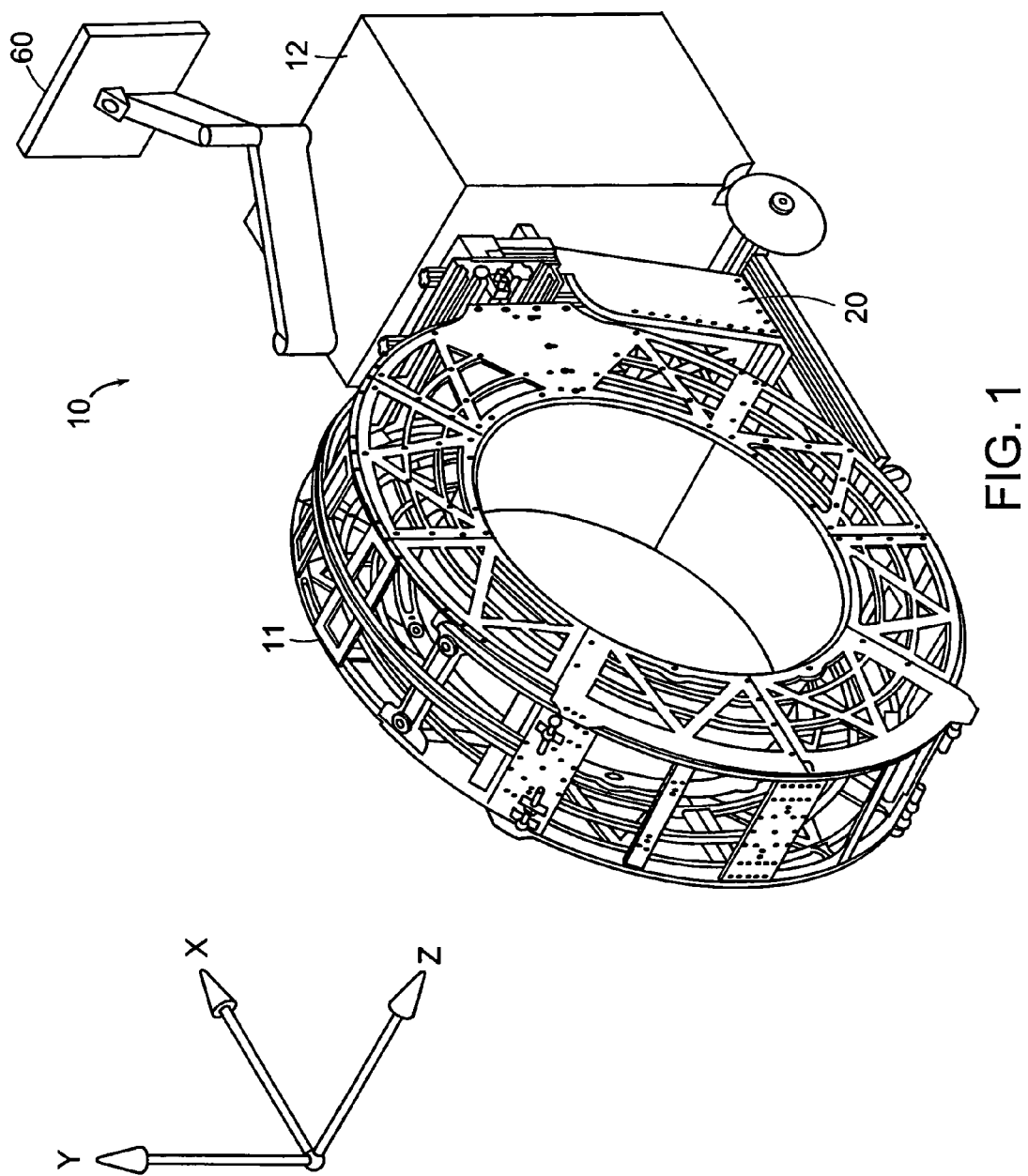
FIG. 1 is a schematic diagram of an x-ray scanning system having gantry positioning apparatus mounted to a cantilevered O-shaped gantry and a mobile cart.

FIG. 1 is a schematic diagram showing an x-ray scanning system 10 in accordance with one embodiment of the invention. The x-ray scanning system 10 includes a gantry 11 secured to a support structure, which could be a mobile or stationary cart, a patient table, a wall, a floor, or a ceiling. As shown in FIG. 1, the gantry 11 is secured to a mobile cart 12 in a cantilevered fashion via a gantry positioning apparatus 20. As described in further detail below, the gantry positioning apparatus 20 can translate and/or tilt the gantry 11 with respect to the support structure to position the gantry 11 in any number of imaging positions and orientations.

The mobile cart 12 of FIG. 1 can optionally include a power supply, an x-ray power generator, and a computer system for controlling operation of the x-ray scanning device and for performing image processing, storage of x-ray images, or other data processing functions. In a preferred embodiment, the computer system controls the positioning apparatus 20 to enable the gantry 11 to be quickly moved to a particular user-defined position and orientation. The computer preferably has a memory that is capable of storing positioning information relating to particular gantry positions and/or orientations. This stored positioning information can be used to automatically move the gantry to a pre-defined configuration upon demand.

The mobile cart 12 preferably also includes a display system 60, such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system.

It will be understood that one or more fixed units can also perform any of the functions of the mobile cart 12.

According to one aspect, the x-ray scanning system of the invention can be used to obtain two-dimensional planar or three-dimensional computerized tomographic (CT) x-ray images of an object, such as a patient. In the embodiment shown in FIG. 1, the gantry 11 is a generally circular, or "O-shaped," housing having a central opening into which an object being imaged is placed. It will be understood that various other gantry configurations, such as a "C-shaped" gantry, can also be employed. In one embodiment, the gantry 11 contains an x-ray source (such as a rotating anode pulsed x-ray source) that projects a beam of x-ray radiation into the central opening of the gantry, through the object being imaged, and onto a detector array (such as a flat panel digital detector array) located on the opposite side of the gantry. The x-rays received at the detector can then be used to produce a two-dimensional or three-dimensional image of the object using well-known techniques.

The x-ray source is able to rotate around the interior of the gantry 11 in a continuous or step-wise manner so that the x-ray beam can be projected through the object, and through a common isocenter, at various angles over a partial or full 360 degree rotation. The detector array is also rotated around the interior of the gantry, in coordination with the rotation of the x-ray source, so that for each projection angle of the x-ray source, the detector array is positioned opposite the x-ray source on the gantry. The apparatus is thus able to obtain high-quality x-ray images of the targeted object in any projection plane over a partial or full 360 degree rotation.

Figure 2:
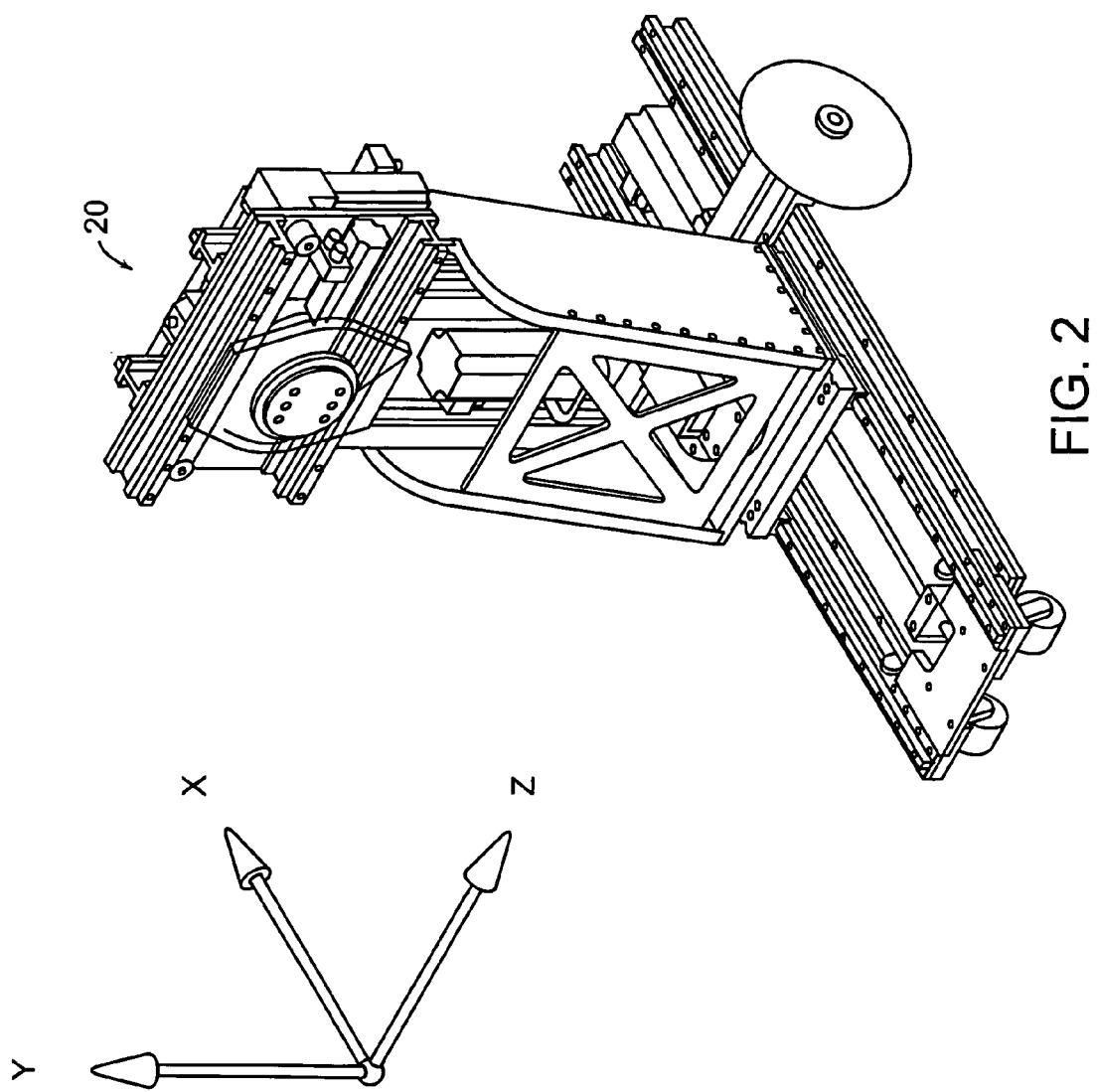
FIG. 2 shows a five degree-of-freedom gantry positioning apparatus.

FIG. 2 illustrates a five degree-of-freedom gantry positioning apparatus 20 according to one aspect of the invention. The positioning apparatus 20 can be connected to a gantry 11 on one side, securing the gantry to the a mobile cart 12 or other support in a cantilevered fashion. In a preferred embodiment, the positioning apparatus 20 is robotically controlled, and enables the gantry 11 to translate and rotate with respect to the support structure in five degrees-of-freedom, including translational movement along the x-, y-, and z-axes, and rotational movement around the x- and y-axes. The gantry positioning apparatus 20 can be controlled manually, or, in a preferred embodiment, it is a motorized system that can be moved electro-mechanically to a desired position. A computerized motion control system can be attached to motorized components of the positioner and one or more discreet positions and orientations of the gantry may be stored in the computer's memory. During operation of the scanning system, pre-defined gantry positions and orientations may be returned to quickly and easily.

Figure 3:
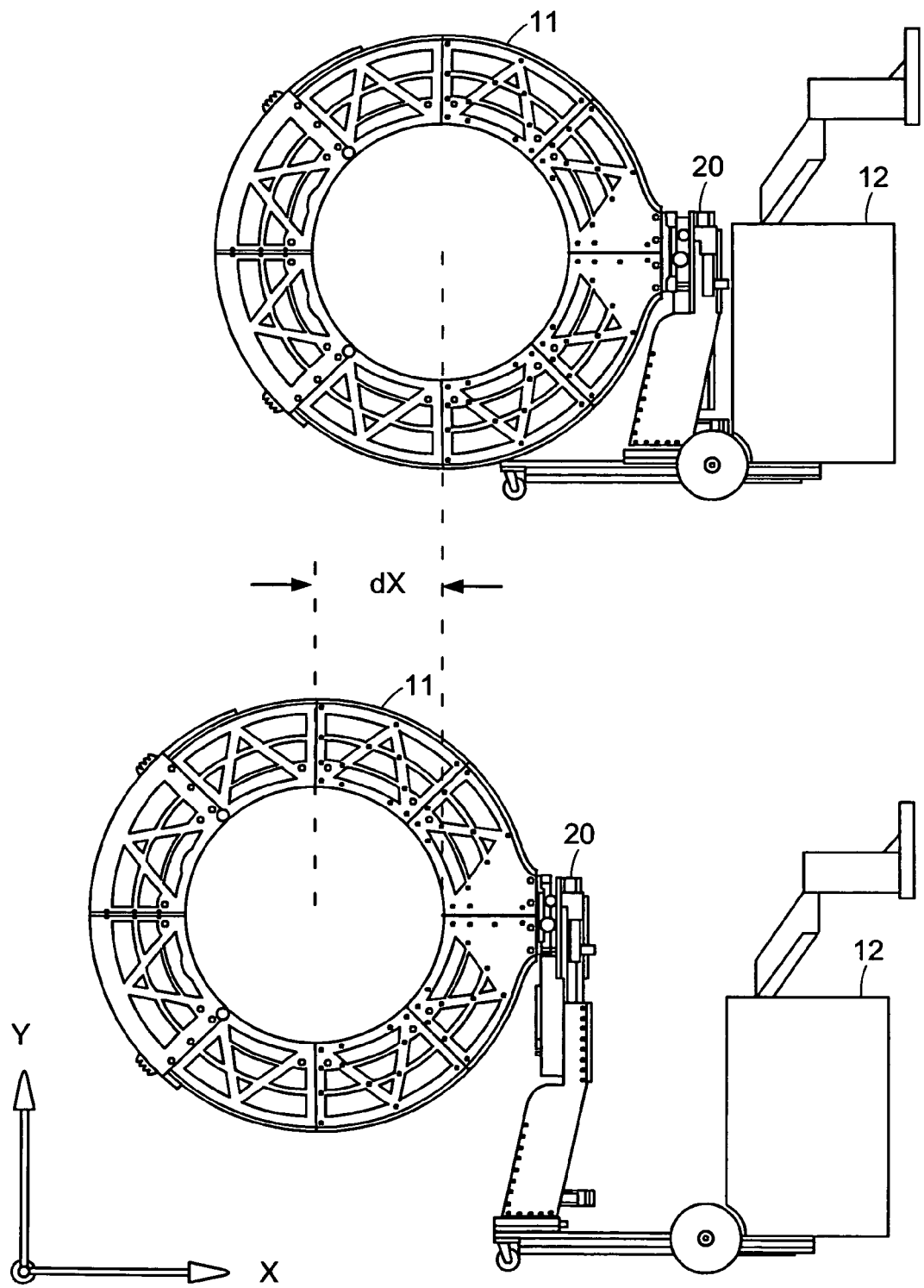
FIG. 3 shows a gantry positioning apparatus translating a gantry ring along the x-axis.
Figure 4:
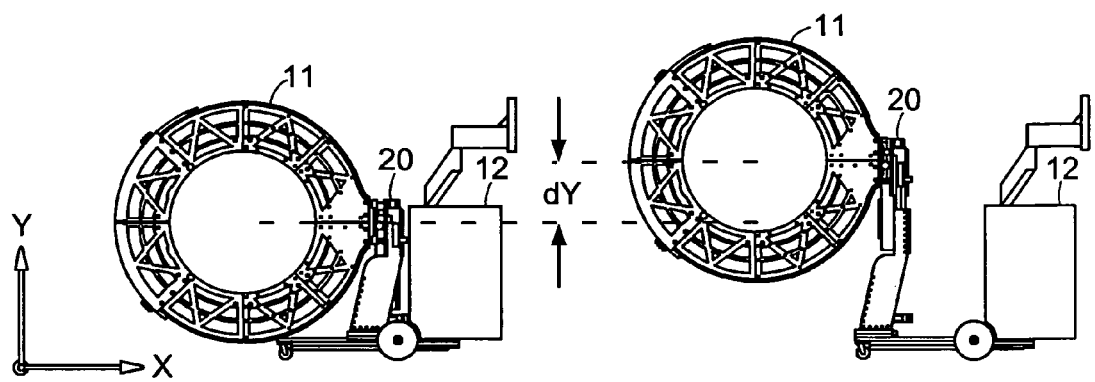
FIG. 4 shows a gantry positioning apparatus translating a gantry ring along the y-axis.
Figure 5A:
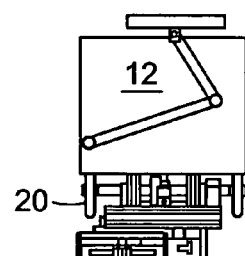
FIGS. 5A-5C shows a gantry positioning apparatus translating a gantry ring along the z-axis.
Figure 5B:
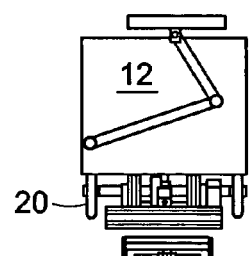
Figure 5C:
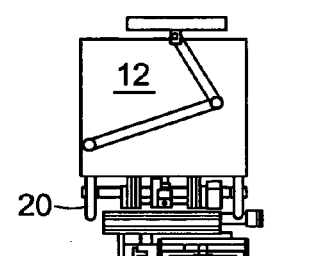

The various translational motions of the gantry positioning apparatus are illustrated in FIGS. 3-5. FIG. 3 is a side view of the scanning system which shows the gantry positioning apparatus 20 translating the gantry a distance dX in the direction of the x-axis. FIG. 4 is a side view of the scanning system which shows the gantry positioning apparatus 20 translating the gantry a distance dY in the direction of the y-axis. FIG. 5 is a top view of the scanning system which shows the gantry positioning apparatus 20 translating the gantry in the direction of the z-axis, from a first position a distance dZ to the left of the center position, to the center position, and then to a third position a distance dZ to the right of the center position.

FIGS. 6 and 7 illustrate the rotational motions of the gantry positioning apparatus 20, according to one aspect of the invention. FIG. 6 is a head-on view of the scanning system which shows the gantry positioning apparatus 20 rotating the gantry about the x-axis of the system. This "tilt" rotational movement is iso-centric, such that the center of the image volume of the gantry remains fixed while the gantry rotates about the x-axis.

FIG. 7 is a top view of the scanning system which shows the gantry positioning apparatus 20 rotating the gantry about the y-axis of the system. According to one aspect, the positioning apparatus 20 is able to achieve true iso-centric "wag" rotation of the gantry about the y-axis via a combination of rotational and translational movements. This is illustrated in FIGS. 8A-8C. In this embodiment, the gantry positioning apparatus 20 connects to the gantry on one side, such that the gantry 13 is free to rotate about a point of rotation 800. This rotational movement is about an axis that is parallel to the y-axis of the gantry. However, because this rotational movement is not collinear with the y-axis of the gantry, this rotational movement results in a translation of the gantry iso-center 801 in the XZ-plane. As illustrated in FIGS. 8A-C, rotating the gantry through an angle, $\theta$, causes the isocenter of the gantry to translate a distance dZ in the direction of the z-axis, and dX in the direction of the x-axis. To compensate for this translational movement, and thus simulate true iso-centric "wag" rotation, the positioning apparatus 20 translates the gantry back into alignment in the directions of the x- and z-axes, respectively, as shown in FIG. 6. As illustrated in FIG. 8B, the distance of the z-axis translation, dZ, required to bring the iso-center 801 back to its original position is $dZ=R*\tan(\theta)$, where R is the radius of the gantry. As shown in FIG. 8C, the distance of the x-axis translation, dX, required to bring the isocenter 801 back to its original position is $dX=R[\tan(\theta)\sin(\theta)+\cos(\theta)-1]$, where R is the radius of the gantry. For any angle of gantry rotation, $\theta$, the distances of the z- and x-axis translations required to bring the iso-center back to its original position, and thus simulate true y-axis rotation, can be determined by a system controller, which can automatically control the positioning apparatus 20 to perform the appropriate translational corrections.

Co-pending U.S. patent application Ser. No. 10/392,365, filed on Mar. 18, 2003, the entire teachings of which are incorporated herein by reference, describes systems and methods for imaging relatively large objects using relatively small detector arrays. This application describes obtaining a large "effective" field of view in a radiation imaging system by a detector positioner that translates a detector array relative to the radiation source in a direction that is substantially normal to the trajectory of the radiation beam.

According to one aspect, the gantry positioning apparatus 20 of the present invention is able to obtain large "effective" fields-of-view by controlling the translational and/or rotational motion of a gantry relative to an object being imaged. As shown in FIG. 5, for example, the gantry positioning apparatus 20 is able to extend the field-of-view of the imaging system in an axial, or longitudinal direction, by translating the gantry 11 in the direction of the z-axis. Three 2D planar or 3D CT object images can be obtained in sequence: a first image with the gantry (and thus the detector) translated a distance dZ to the left of center, a second image with the gantry and detector at the center position, and a third image with the gantry and detector translated a distance dZ to the right of center. The three sequentially obtained images can then be combined, or "stitched" together, to produce an image having a wider axial field-of-view than is obtainable using a single, fixed detector. This technique advantageously permits near-simultaneous imaging of objects which would otherwise extend outside the gantry field-of-view in a lengthwise direction, such as a human spine.

FIG. 9 illustrates a method for obtaining a wide-angle 2D anterior/posterior object image by rotating the gantry about the focal spot 900 of the radiation source 13. This method can be used when the source 13 is at the top position of the gantry, and the detector 14 is at the bottom, or when the detector 14 is at the top position and the source 13 is at the bottom, in what is commonly known as an anterior/posterior (AP) configuration. The positioning apparatus 20 simulates rotation about the focal spot 900 of the source by rotating the gantry about the x-axis, and then correcting for translational movement of the focal spot 90Q in the YZ-plane by translating the gantry in the y-axis and z-axis directions until the focal spot 900 returns to its original position. This technique of one rotational movement and two corrective translations is analogous to the y-axis "wag" rotation described in connection with FIGS. 7 and 8A-8C. As shown in FIG. 9, this technique of simulating rotation of the gantry about the focal spot 900 of the source 13 enables the scanner to sequentially obtain multiple anterior/posterior images at different detector positions, and then digitally "stitch" together the resultant data to produce an effectively large field-of-view AP image.

FIG. 10 shows this same technique applied to obtain effectively large field-of-view 2D lateral object images. Here, the source and detector both lie on the x-axis of the gantry (i.e. in a lateral position). The gantry positioning apparatus pivots the gantry about the y-axis, and translates in the XZ-plane, to simulate rotation about the x-ray focal spot 900. This enables the scanner to sequentially obtain multiple lateral object images at different detector positions, and then digitally "stitch" together the resultant data to produce an effectively large field-of-view lateral image.

This method of obtaining effectively large 2D object images can be generalized to any configuration of a gantry positioning apparatus and gantry in which the radiation source and detector are positioned opposite one another on the gantry such that the line connecting the source and the detector is perpendicular to an axis of rotation of the gantry. In this way, the gantry positioning apparatus can rotate and translate the gantry to approximate rotation about the focal spot of the radiation source, and thus generate a wide-angle 2D object image.

Figure 11:
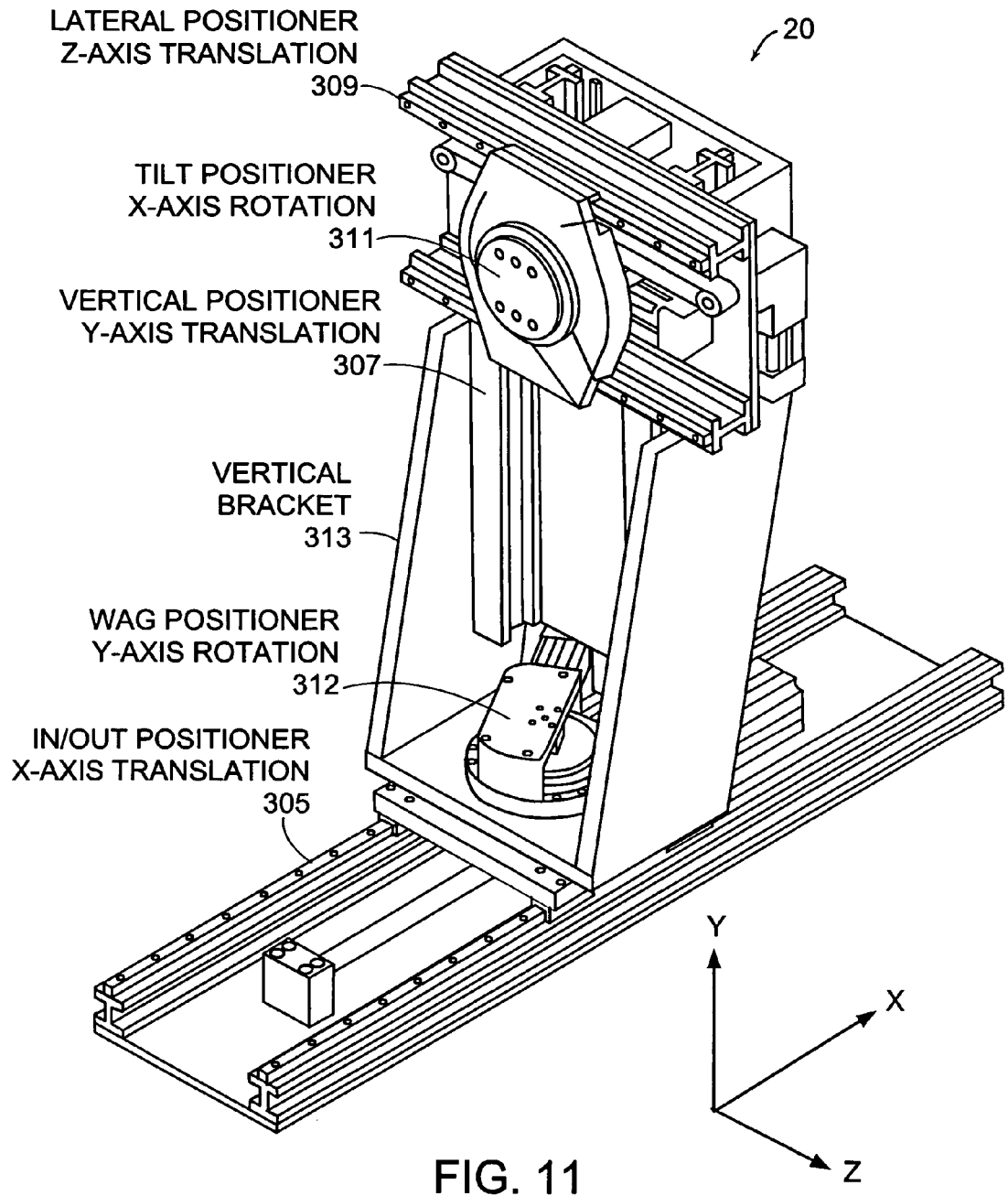
FIG. 11 illustrates the positioning stages of a gantry positioning apparatus for effecting translational and rotational movement.

Turning now to FIG. 11, a five degree-of-freedom gantry positioning apparatus 20 is shown in detail. In the embodiment illustrated, the apparatus 20 comprises three linear positioning devices, including an in/out positioner 305 for x-axis translation, a vertical positioner 307 for y-axis translation, and a lateral positioner 309 for z-axis translation. The apparatus 20 further comprises two rotational positioning devices, including a tilt positioner 311 for x-axis rotation, and a wag positioner 312 for effecting y-axis rotation. The various positioning devices are mounted on a vertical mounting bracket 313. The various components of the positioning apparatus 20 are shown in a disassembled view in FIG. 12. As illustrated here, the wag positioner 312 connects on one end to the in/out positioner 305, and on the other end to the vertical bracket 313. This permits the in/out positioner 305 to translate the upper portion of the positioning apparatus and the gantry in the direction of the x-axis. The wag positioner 312 is able to rotate the entire bracket 313, as well as the gantry, about a vertical axis relative to the in/out positioner and the support structure. The bracket 313 is attached to one portion of the vertical positioner 307, while a second portion of the vertical positioner 309, along with the gantry, is movable in a vertical direction relative to the bracket and to the support structure. The movable portion of the vertical positioner 309 attaches to one portion of the lateral positioner 311, while a second portion of the lateral positioner 311, along with the gantry, is movable in a lateral direction relative to the bracket and the support structure. Finally, the tilt positioner 311 is secured to the movable portion of the lateral positioner 311, while the portion of the tilt positioner 311 which mounts the gantry to the apparatus 20, rotates the gantry about the x-axis relative to the support structure.

Figure 13:
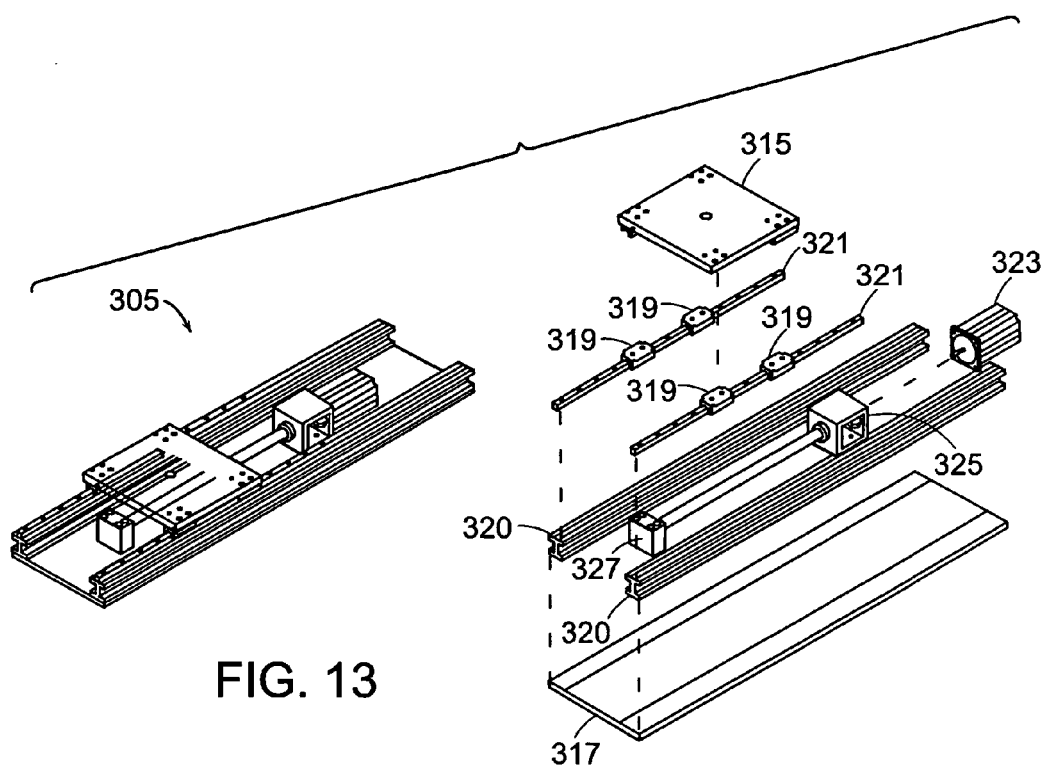
FIG. 13 shows the positioning apparatus for x-axis translation.

Turning now to FIG. 13, the in/out positioner 305 for x-axis translation comprises a motorized assembly for translating the cantilevered gantry ring towards or away from the support structure. The in/out positioner includes a top plate 315 upon which the wag rotational positioner 312 (see FIG. 11) is bolted. The top plate 315 is movable along the length of a base plate 317 via blocks 319 which mate with linear guide rails 321 mounted on rail mounts 320 which are attached to the base plate 317. A geared servo motor 323 is rigidly attached to the base plate 317 by a motor mount 325. A ball screw assembly 327 is mounted to the base plate 317, and runs along the length of the base plate 317 parallel to linear guide rails 321. The ball screw assembly includes a ball screw mated with a ball screw nut. The nut is fixedly secured to the top plate 315. The motor 323 rotates the ball screw in a clockwise or counterclockwise direction via motor shaft coupling. The rotation of the ball screw, in either a clockwise or counterclockwise direction, causes the ball screw nut, and thus the top plate 315, to travel up and down the length of the ball screw. The linear guide and blocks steer the top plate as it is displaced along the length of the base plate 317 by servo motor 323. In this way, the cantilevered gantry assembly can be translated towards or away from the support structure, such as a mobile cart, floor, wall, ceiling, or a patient table, in a controlled manner.

Figure 14:
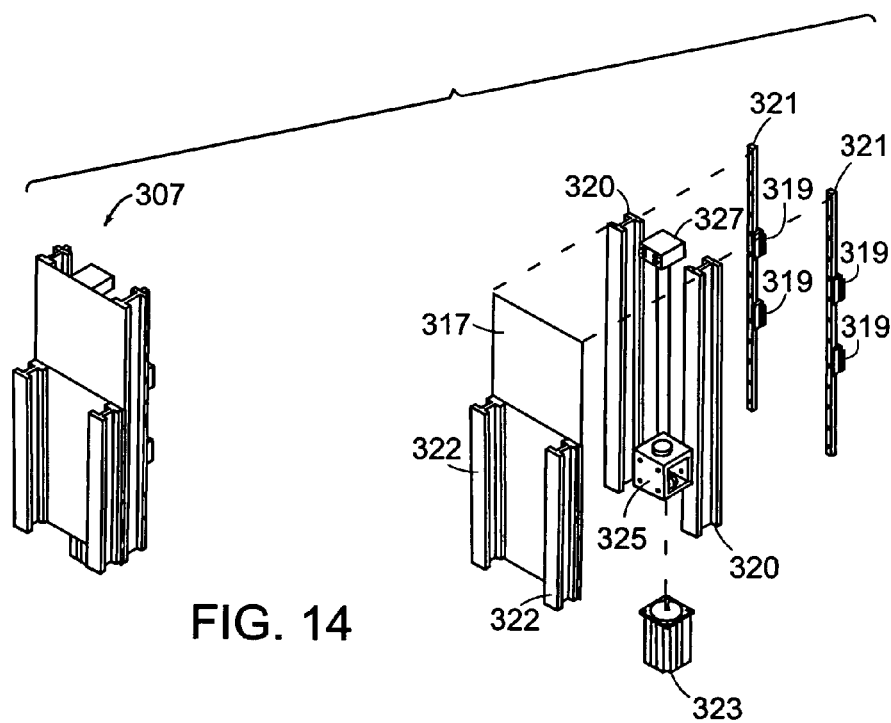
FIG. 14 shows the positioning apparatus for y-axis translation.

FIG. 14 shows the vertical positioner 307 for translating the cantilevered gantry vertically relative to the support structure. In the embodiment shown in FIG. 14, the vertical positioner 307 is a motorized assembly that is essentially identical to the in/out positioner 305 in terms of its structure and operation. However, the vertical positioner 307 is oriented vertically so that the blocks 319 can be translated upwards or downwards relative to the base plate 317. As illustrated in FIG. 14, the vertical positioner includes a set of blocks 319 which ride on linear guide rails 321 mounted on rail mounts 320 which are attached to one side of the base plate 317. The blocks 319 are translated relative to the base plate 317 by a servo motor 323 and ball screw assembly 327, as described in connection with FIG. 13. One the other side of the base plate 317 is a second set of rail mounts 322. These rail mounts 322 are used to guide the vertical positioner 307 as it moves up and down relative to the vertical mounting bracket 313, as shown in FIG. 11. The blocks 319 and the nut of the ball screw assembly 327 of the vertical positioner 317 are fixed to the rear wall of the mounting bracket 313. Thus, as the motor 323 and ball screw assembly 327 linearly translate the nut relative to the base plate 317, the base plate 317, guided by blocks 319, moves vertically up and down relative to the bracket 313.

Figure 12:
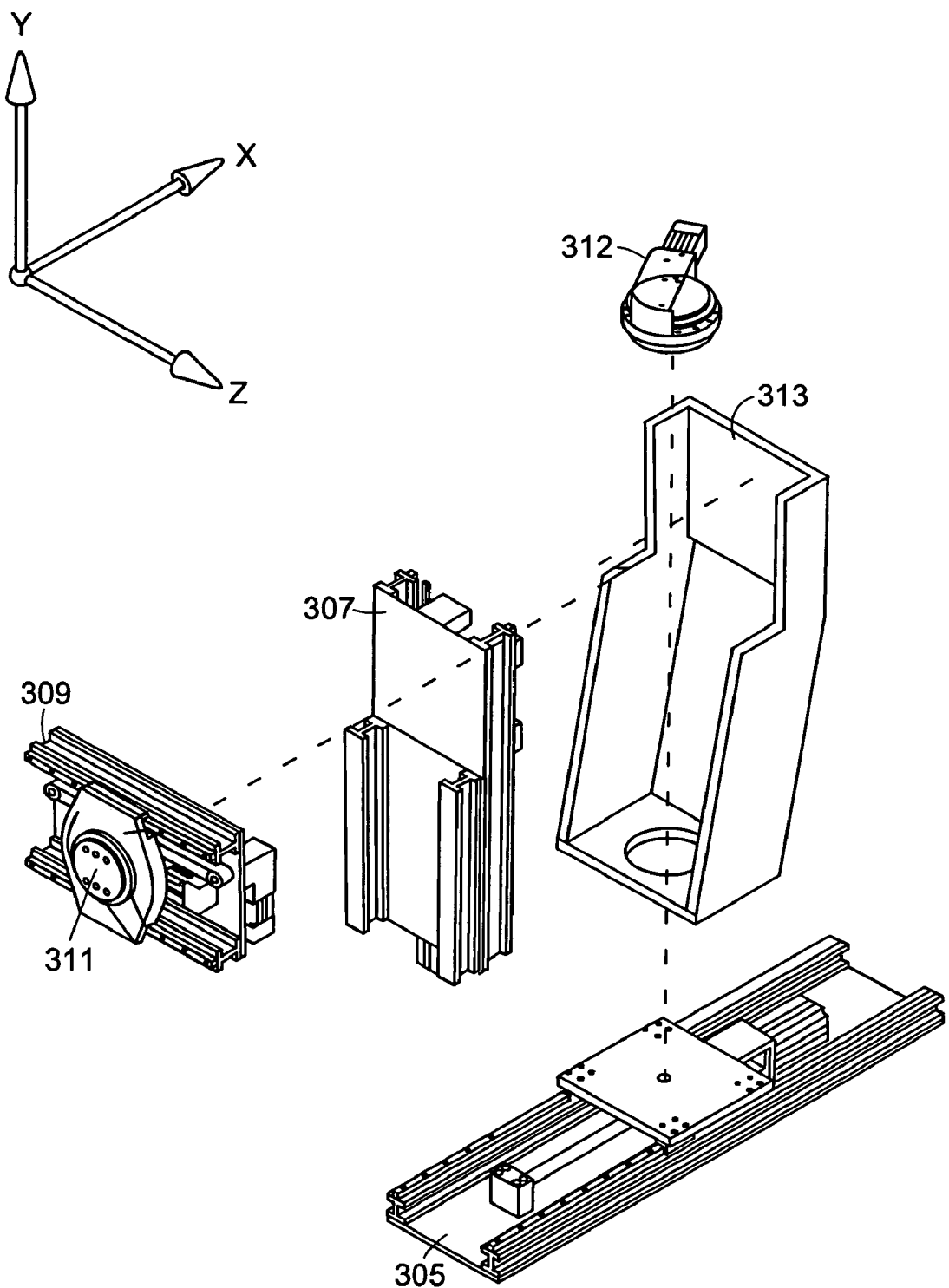
FIG. 12 is an exploded schematic of a five degree-of-freedom gantry positioning apparatus.

FIG. 15 shows the lateral positioner 309 for translating the cantilevered gantry in a lateral direction relative to the support structure. In this embodiment, the lateral positioner 309 comprises a motorized assembly that is oriented in a lateral direction so that the blocks 319 can be translated in the direction of the z-axis relative to the base plate 317. As illustrated in FIG. 15, the lateral positioner includes a carriage plate 344 which is connected to a set of blocks 319 which ride on linear guide rails 321 mounted on rail mounts 320. The rail mounts 320 are rigidly attached to one side of the base plate 317. A geared servo motor 323 and gear box 340 are also attached to base plate 317. The motor 323 gear box 340 are connected to a belt drive assembly 342 having a belt that is movable laterally along the length of the base plate 317. The belt is connected to the carraige plate 344, so that when the belt drive assembly is driven by the motor and gear box, the carriage plate 344, guided by blocks 319, translates in a lateral direction relative to the base plate 317. As shown in FIG. 12, the base plate of the lateral positioner 309 is rigidly attached to the base plate of the vertical postioner 307. The entire lateral positioner 309 is thus translated in/out or vertically up/down with the respective movements of the in/out positioner 305 and the vertical positioner 307. The carriage plate of the lateral positioner 309 can be attached to the gantry ring to translate the ring laterally left and right relative to the bracket 313 and the support structure.

Figure 16:
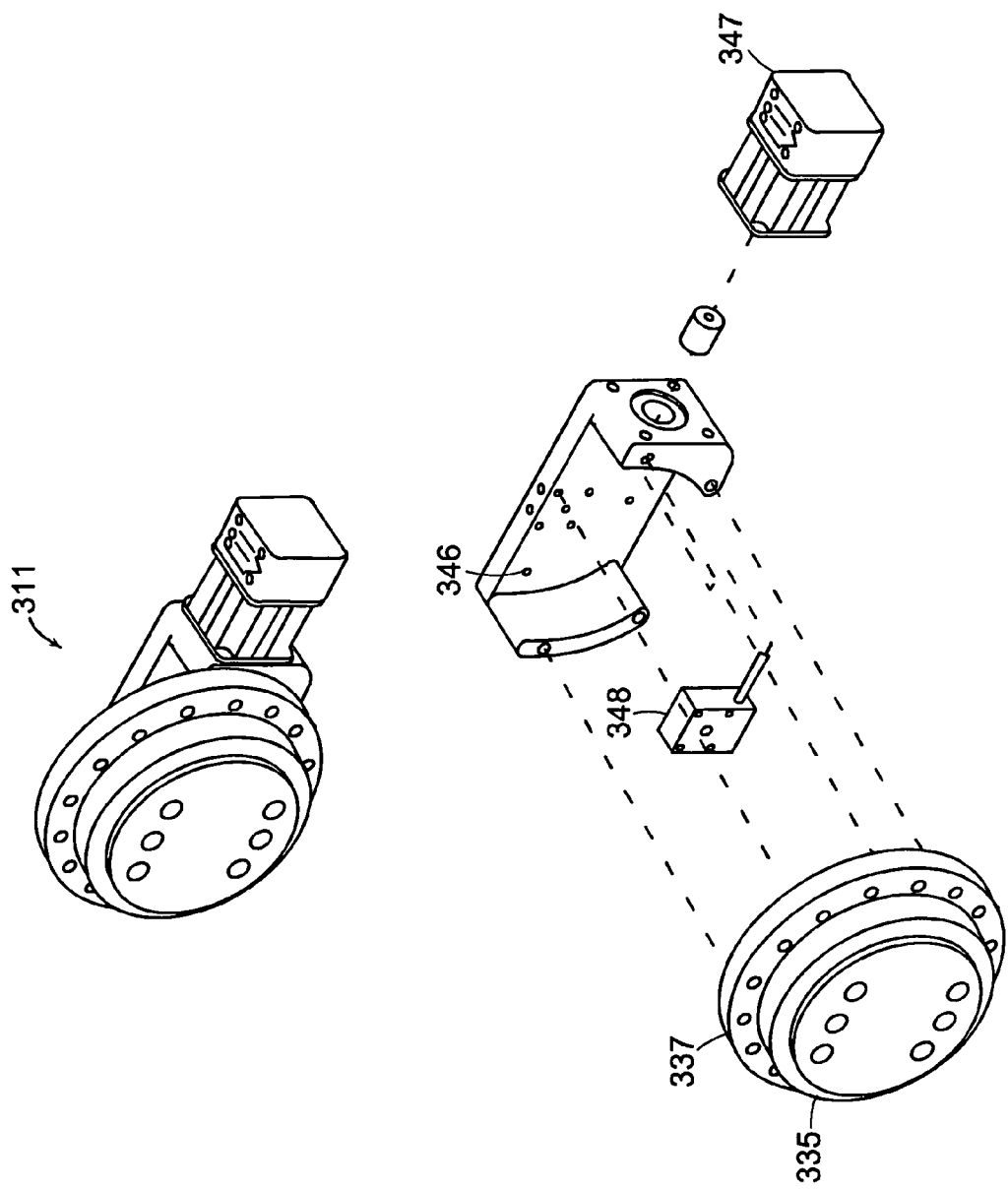
FIG. 16 shows the positioning apparatus for rotational movement about an axis.

FIG. 16 shows a rotational positioner for rotating the cantilevered gantry relative to the support structure. One such rotational positioner can be used as the tilt positioner 311 for x-axis gantry rotation, and a second rotational positioner can be used as the wag positioner 312 for effecting y-axis gantry rotation. A bearing with an inner ring 335 rotates relative to an outer ring assembly 339 larger in diameter than the inner ring. The outer ring 339 is rigidly attached to an interface plate 346. The inner ring 335 is driven by a geared servo motor 347 and gearbox 348, and is rotatable with respect to the outer ring 339. When the rotational positioner is used as the x-axis tilt positioner 311, the outer ring 339 is secured to the carriage plate 344 of the lateral positioner 309, and the inner ring 335 can then be secured to the gantry, as indicated in FIG. 15, thus enabling the gantry to tilt with respect to the rest of the gantry positioner and the fixed support structure. When the rotational positioner is used as the y-axis wag positioner 312, the inner ring 335 is secured to the top plate 315 of the in/out positioner 305, and the outer ring 339 is secured to the vertical mounting bracket 313, as indicated in FIG. 12, thus enabling the upper portion of the gantry positioning apparatus, and the gantry itself, to rotate about a vertical axis with respect to the in/out positioner 305 and the support structure.

According to one aspect, each of the positioner assemblies 305, 307, 309, 311, and 312 comprising the gantry positioning apparatus 20, includes a mechanism for providing position feedback information to its respective servomotor in order to enable precise positioning of the gantry along each degree of translational or rotational motion. For example, referring to FIG. 13, a linear encoder tape can be affixed to a linear guide rail 321, and a read head can be located on a the top plate 315 for reading the encoder tape and providing feedback data indicative of the relative positions of the top plate 315 and the base plate 317. Similarly, in reference to FIG. 16, a rotary encoder can be used to determine the relative angular positions of the inner 335 and outer 339 rings. Preferably, the position feedback mechanism is an absolute position encoder system, so that, at any given time, a computerized motion control system can precisely determine the translational and/or rotational position of the ring positioning unit in all degrees of freedom, and can thus determine the position and orientation of the gantry in three-dimensional space.

Figure 17:
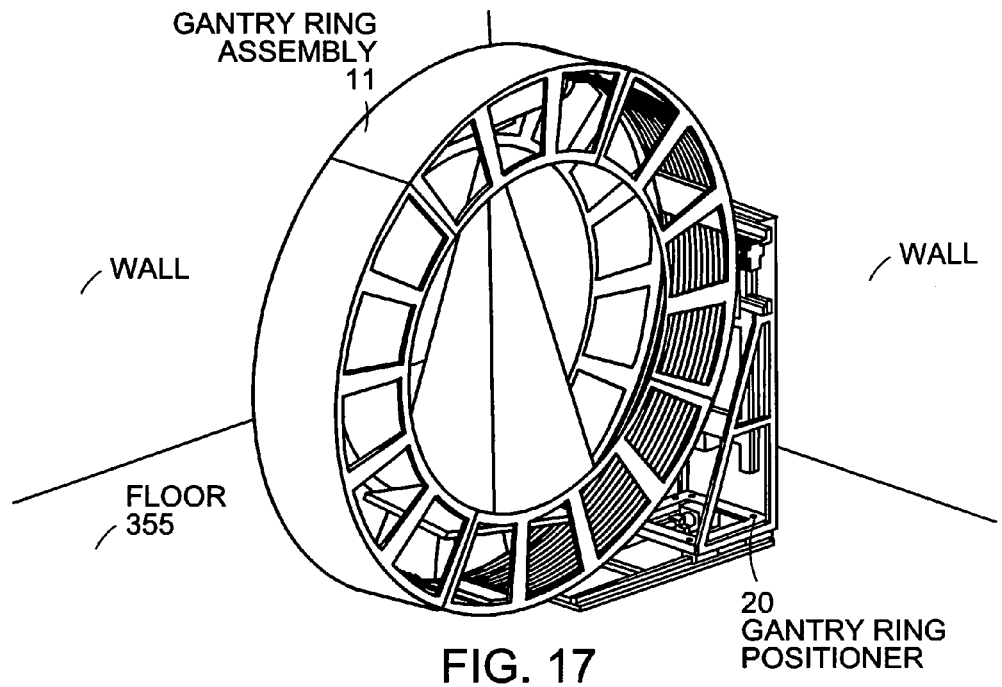
FIG. 17 shows a floor-mounted cantilevered gantry ring with gantry positioning apparatus.
Figure 18:
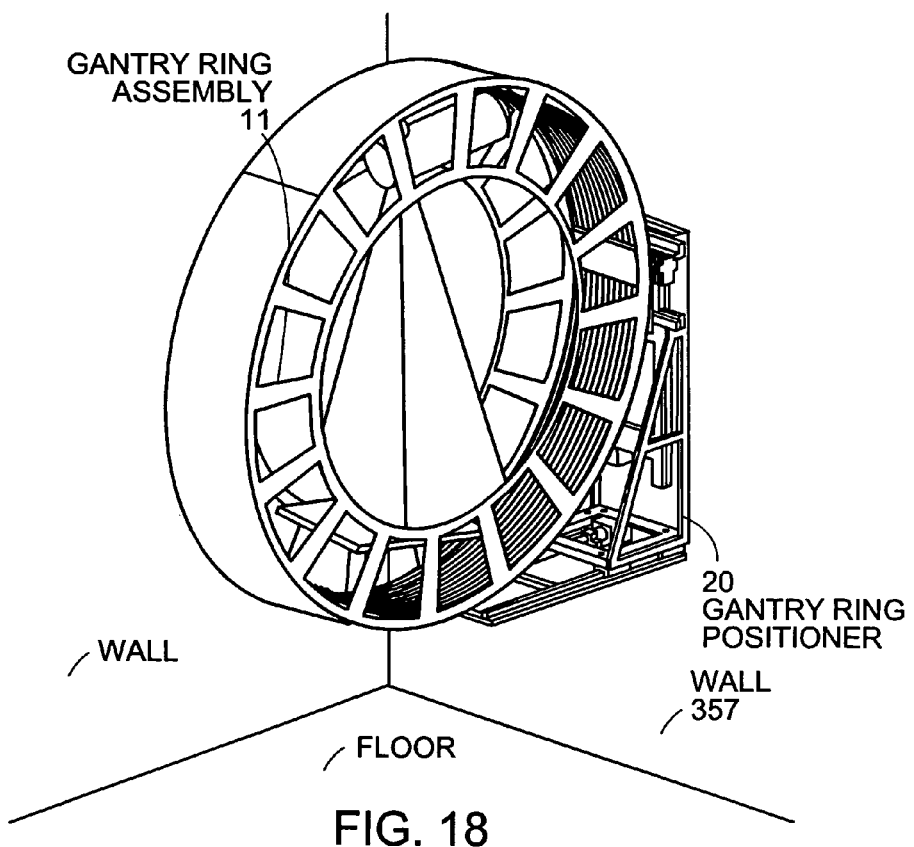
FIG. 18 shows a wall-mounted cantilevered gantry ring with gantry positioning apparatus.
Figure 19:
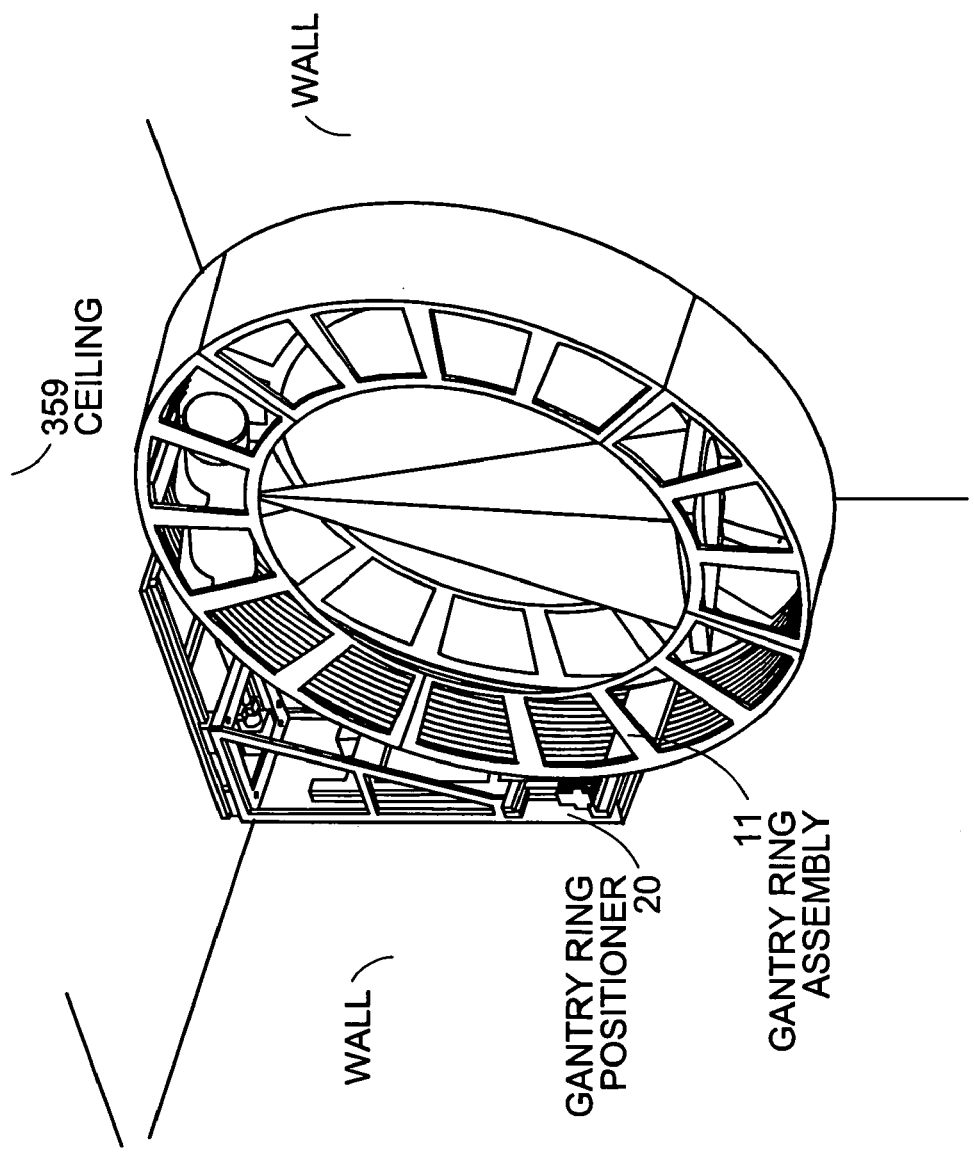
FIG. 19 shows a ceiling-mounted cantilevered gantry ring with gantry positioning apparatus.

Turning now to FIGS. 17-19, various embodiments of a cantilevered gantry 11 and gantry positioning apparatus 20 are shown. In FIG. 17, the gantry positioning apparatus 20 is mounted to the floor 355 by the base plate of in/out positioner 305. The tilt positioner 311 is mounted to one side of the gantry 11. The gantry positioning apparatus is operable to translate and tilt the gantry 11 relative to the fixed room.

FIG. 18 shows the gantry positioning apparatus 20 mounted on one side to a wall 357, and on the other side to the gantry 11, thus allowing the cantilevered gantry to translate and tilt relative to the fixed room. In FIG. 19, the gantry positioning apparatus 20 is fixed on one side to the ceiling 359, and on the other side to the gantry 11. The ring positioning unit 20 and gantry 11 could be similarly mounted to any suitable support structure, such as to a table upon which a patient under examination is placed.

According to yet another aspect, the present invention relates to a radiation imaging system and method for maximizing the field-of-view of the object being imaged which combines a rotation of the radiation source and detector with a translation of the gantry ring in the two orthogonal directions. This method can be implemented using the x-ray scanning system and gantry positioning apparatus previously described in connection with FIG. 1.

Figure 20:
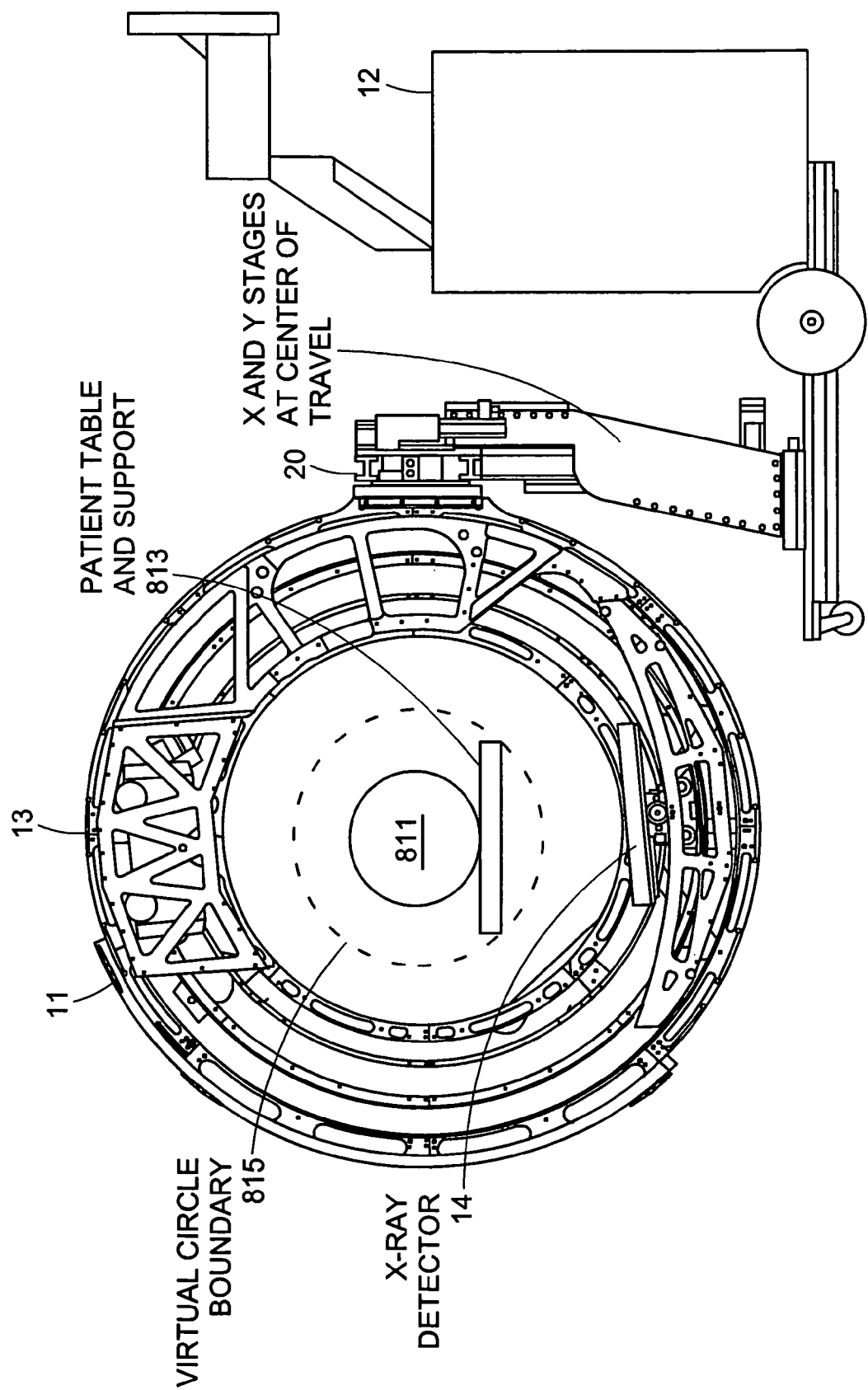
FIG. 20 shows an imaging system with gantry positioning apparatus with a patient centered in the gantry ring.

FIGS. 20-29 illustrate one example of this technique for obtaining a three-dimensional CT object reconstruction with an enlarged field-of-view. As shown in FIG. 20, the scanning system includes a human patient 811 placed inside the gantry 11. The patient 811 is supported on a patient table 813, and is initially centered at the iso-center of the gantry ring 11. The gantry positioning apparatus 20 is partially extended in the x- and y-directions, so that the in/out positioner and vertical positioner are approximately at their respective centers of travel. The x-ray source 13 and detector 14, are rotated inside the gantry to a 0-degree position, such that the source is at top-dead-center of the gantry, and the detector is at the bottom of the gantry, directly underneath the patient.

Figure 21:
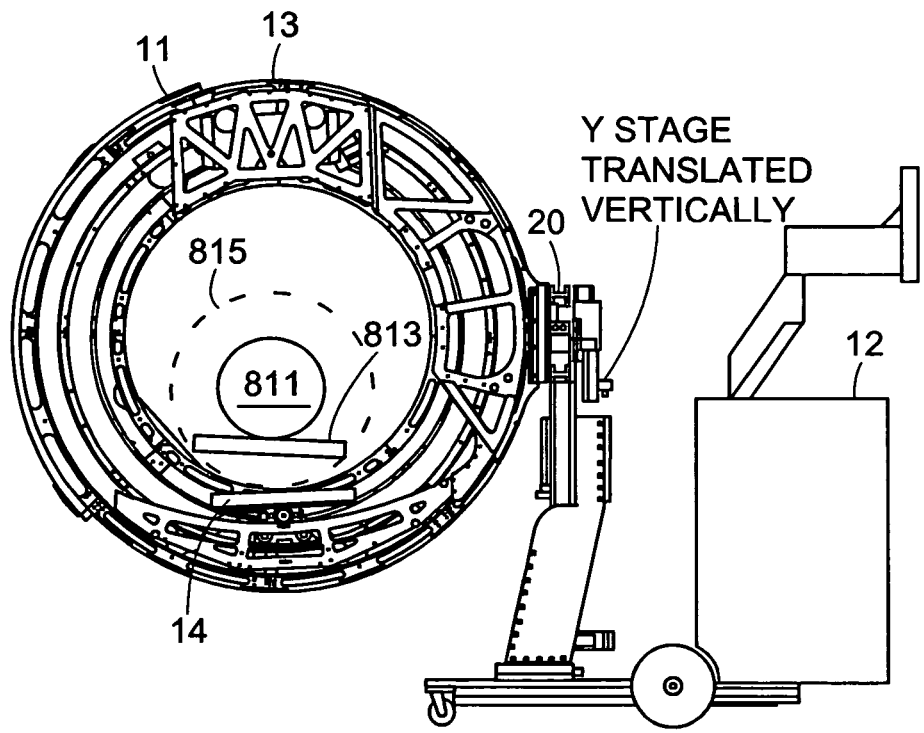
FIG. 21 shows the imaging system with the gantry translated vertically to increase the field-of-view of the detector.

Next, the gantry positioning apparatus 20 translates the gantry 11 vertically upwards in the direction of the y-axis until the inner bore diameter of the gantry is tangent to a virtual circle 815 that is centered on the object being imaged and has a diameter that is slightly larger than the object and any support structure (such as table 813), as is illustrated in FIG. 21. By moving the detector closer to the object being imaged, the field-of-view of the system is increased. Once the gantry is positioned as shown, an x-ray view can be captured to computer memory, and stored for viewing or further processing.

To obtain a 3D CT image, the source and detector are rotated inside the gantry to obtain x-ray data from various projection angles. Preferably, during the rotaional scan around the object, the system maintains the tangency of the gantry bore circle and the virtual circle, so as to maintain the increased field-of-view of the detector. This can be accomplished by controlling the translational movements of the gantry in coordination with the rotation of the detector, as shown in FIGS. 22-28.

Figure 22:
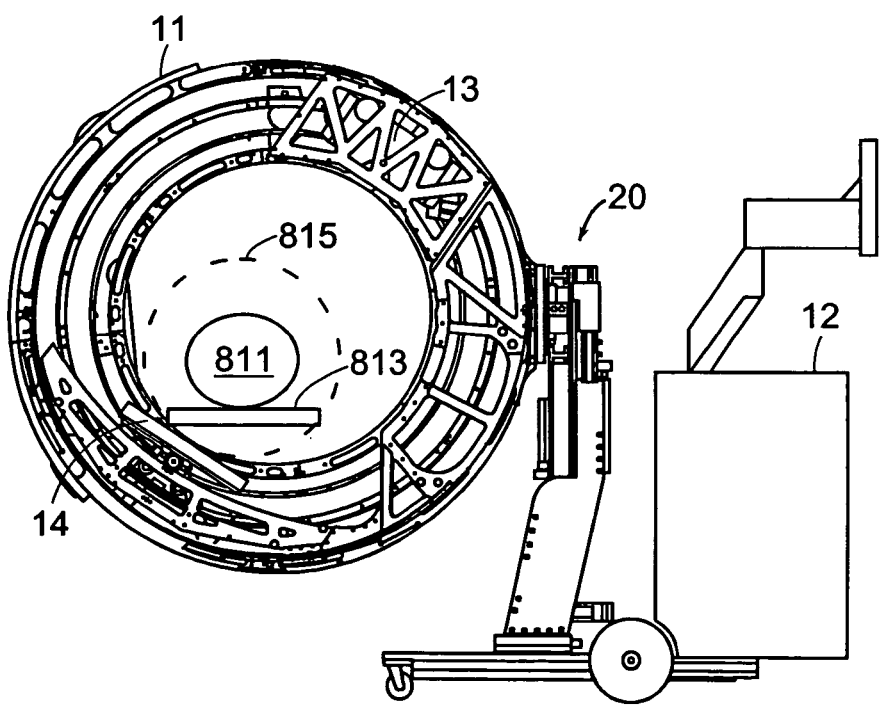
FIG. 22 shows the system of FIG. 21 with the detector rotated to a 45-degree position and the gantry translated to maintain a tangent relationship with a virtual circle surrounding the patient.
Figure 23:
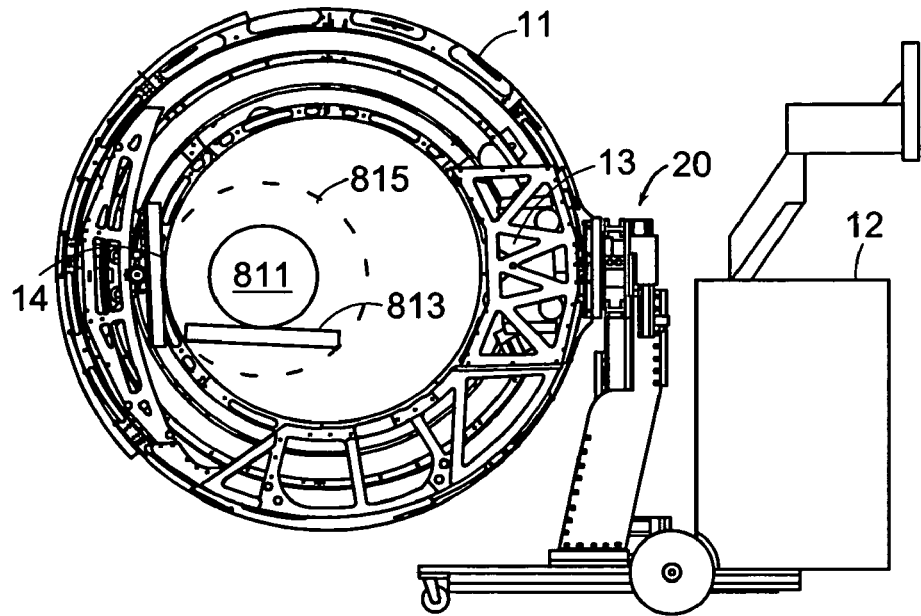
FIG. 23 shows the system of FIG. 21 with the detector rotated to a 90-degree position.
Figure 24:
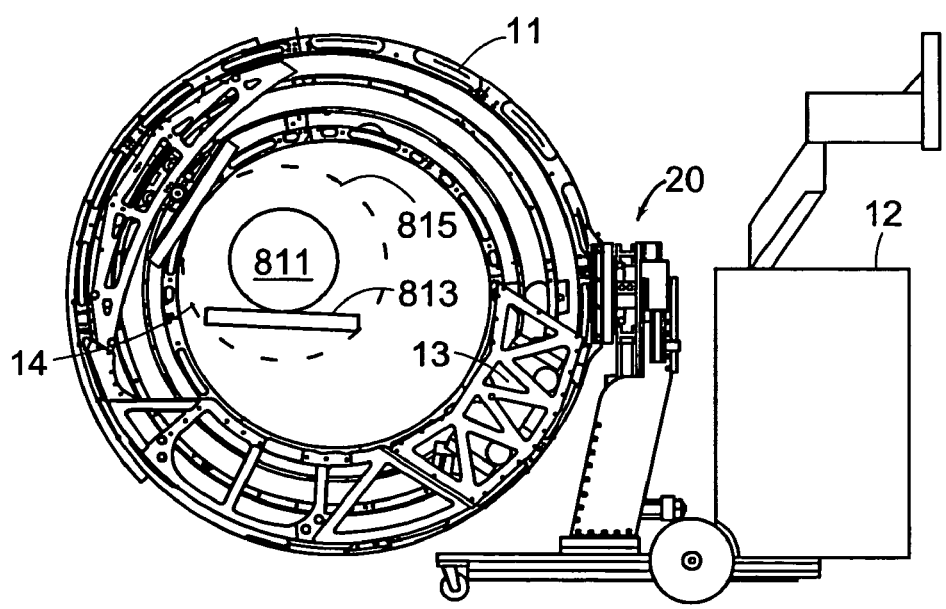
FIG. 24 shows the system of FIG. 21 with the detector rotated to a 135-degree position.
Figure 25:
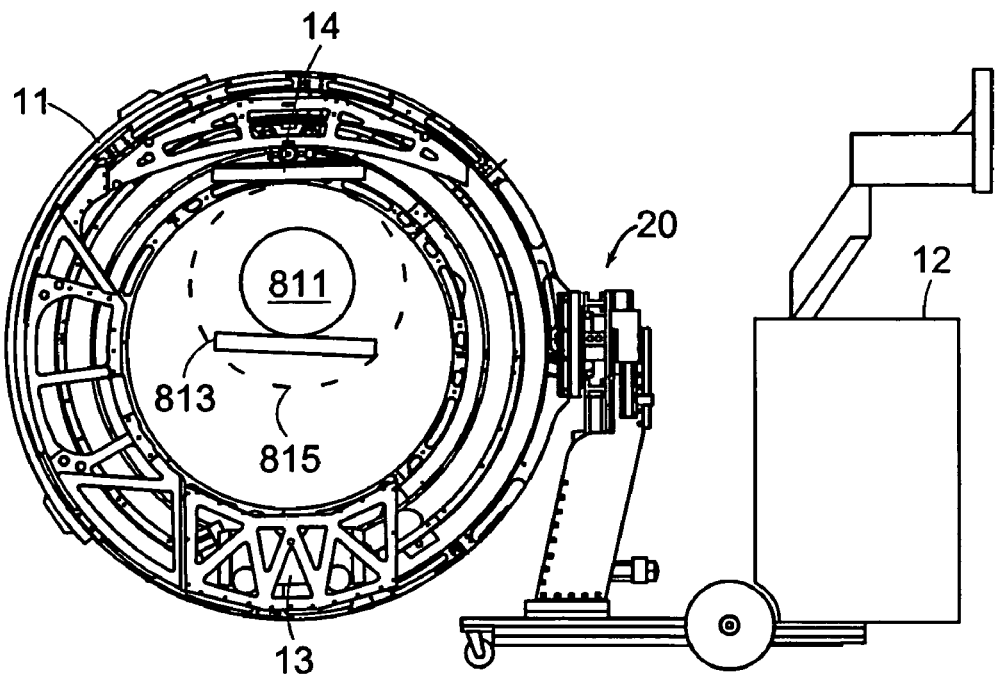
FIG. 25 shows the system of FIG. 21 with the detector rotated to a 180-degree position.
Figure 26:
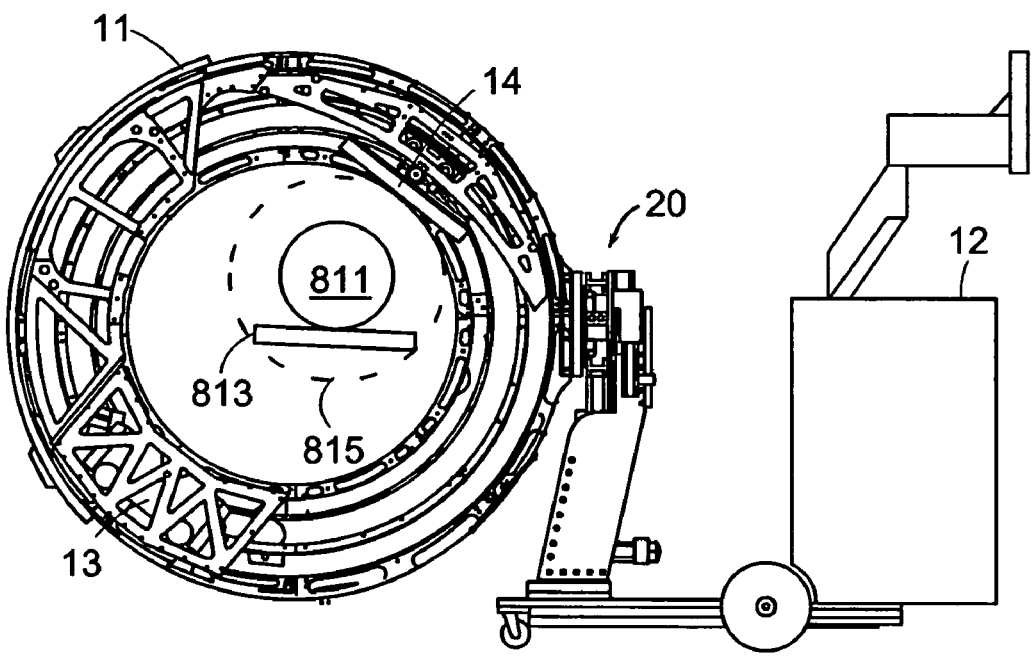
FIG. 26 shows the system of FIG. 21 with the detector rotated to a 225-degree position.
Figure 27:
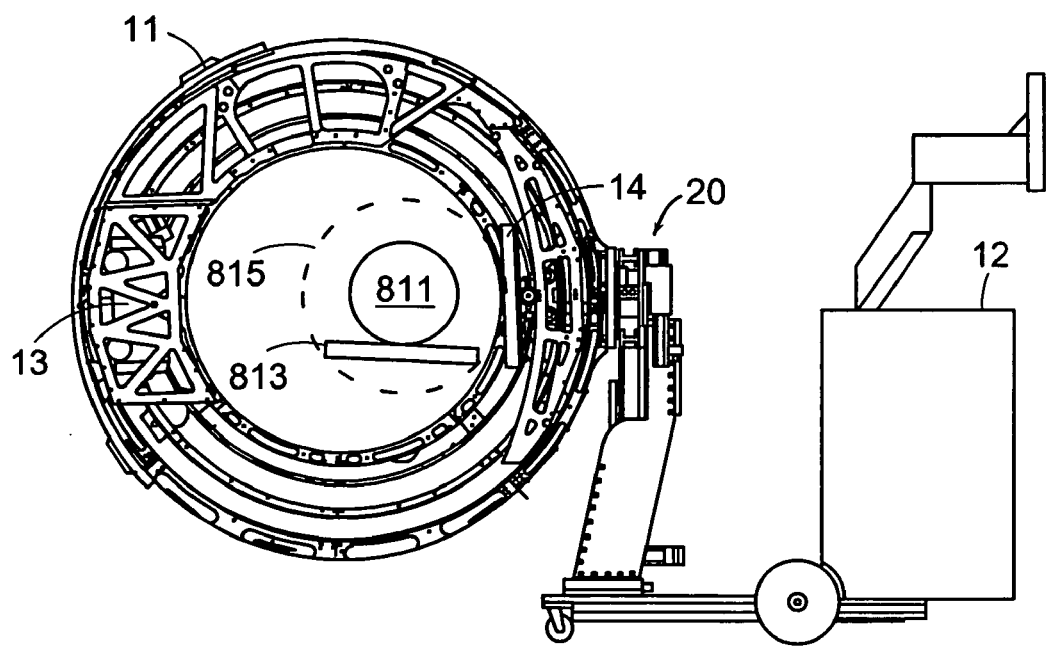
FIG. 27 shows the system of FIG. 21 with the detector rotated to a 270-degree position.
Figure 28:
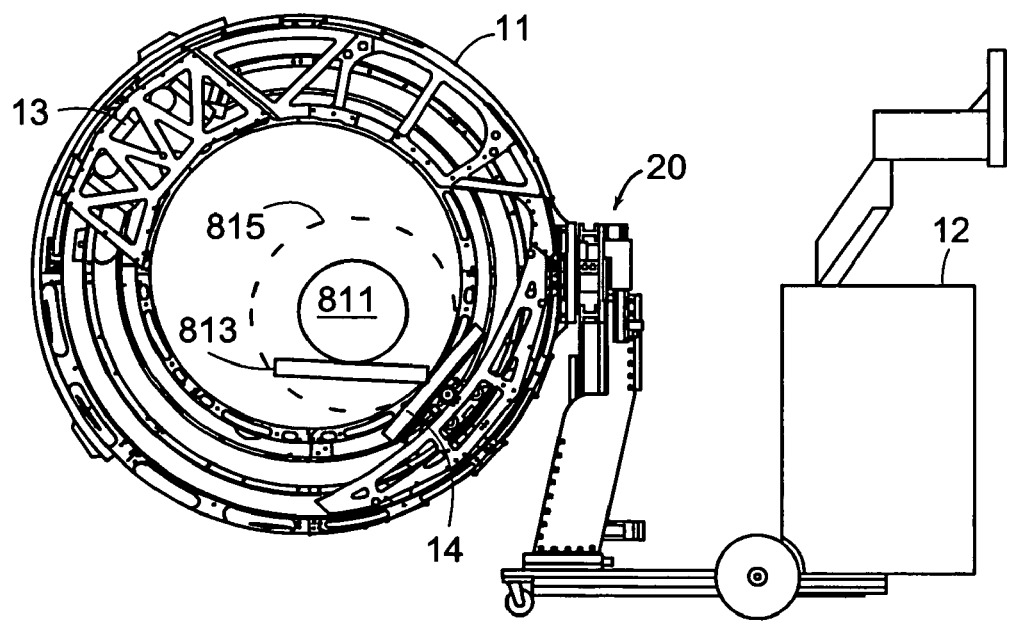
FIG. 28 shows the system of FIG. 21 with the detector rotated to a 315-degree position.
Figure 29:
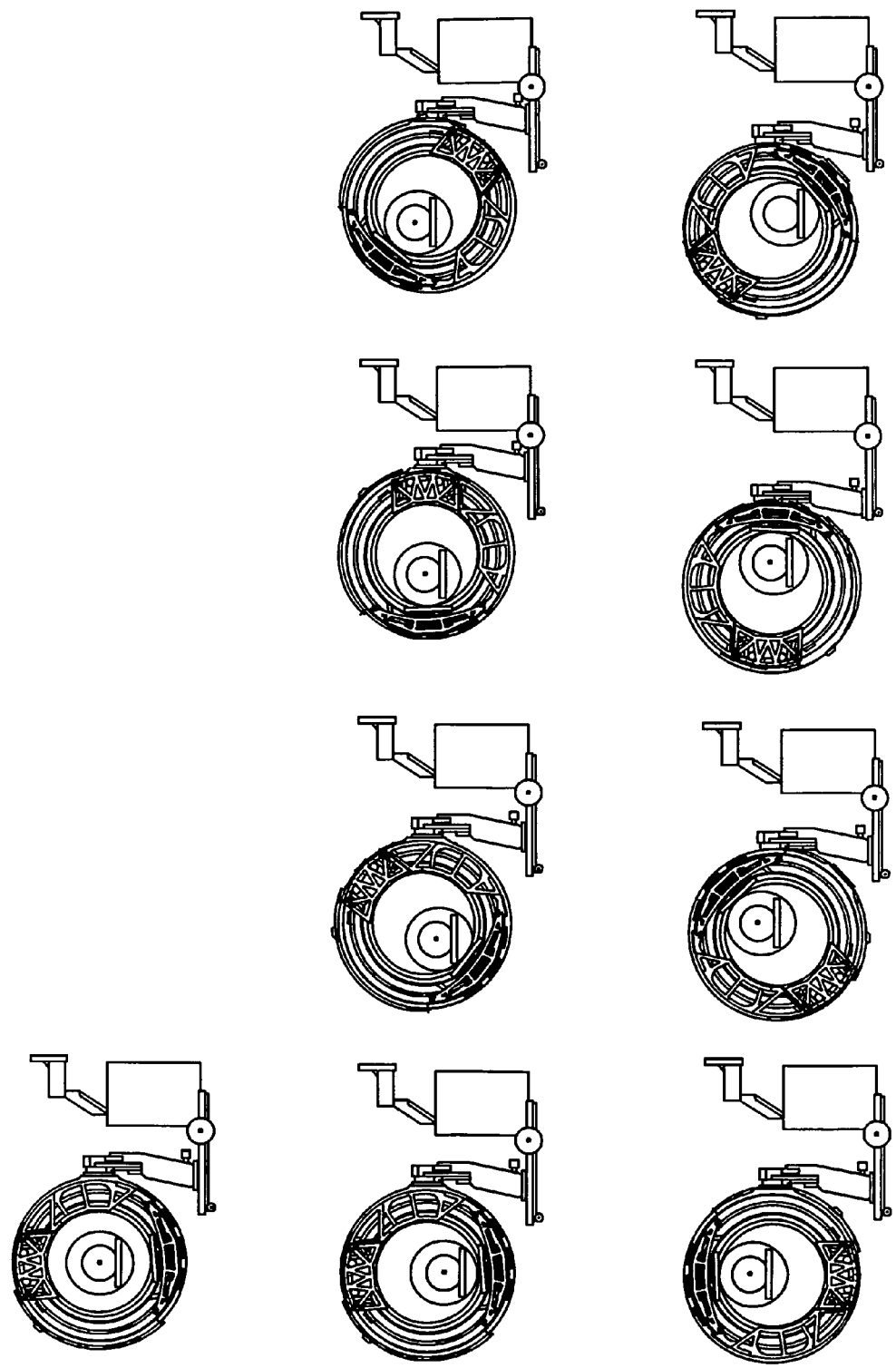
FIG. 29 shows a "hula-hoop" data collection matrix for obtaining large field-of-view CT images.

For instance, as shown in FIG. 22, the detector 14 has moved from the 0-degree position to a 45-degree position on the gantry. As the detector rotates, the gantry positioning apparatus 20 translates the gantry a first distance in the direction of the x-axis, and a second distance in the direction of the y-axis so that the inner bore of the gantry at the location of the detector remains tangent to the virtual circle 815 surrounding the patient and the support table. This process is repeated as the detector rotates to 90-degrees (FIG. 23), 135-degrees (FIG. 24), 180-degrees (FIG. 25), 225-degrees (FIG. 26), 270-degrees (FIG. 27), and 315-degrees (FIG. 28). At each subsequent rotational position of the detector and source, (or at least in each position at which x-ray projection data is obtained), the gantry positioning apparatus 20 translates the gantry in the x- and y-axes to maintain the tangency of the detector 14 with the virtual circle 815. When the detector has rotated a full 360-degrees, and returns to the 0-angle position, the gantry translates back to its original position shown in FIG. 21. The gantry 11 thus continually moves in the XY plane, in coordination with the rotational movement of the detector, to maintain the tangency of the gantry at the detector position with the virtual circle defined by the object and support structure. This multi-axis translational movement of the gantry relative to the virtual circle is analogous to the movement of a "hula-hoop" about the torso of a person. For each x-ray exposure of the detector, the rotational angle of the source and detector, and the gantry translational positions, are recorded. The stored gantry positions are then fed into a CT algorithm to produce a three-dimensional object reconstruction. Because of the "hula-hoop" translations of the gantry, the field-of-view of the reconstructed image is larger than the image would be with a conventional iso-centric gantry scan. A subset of the CT data collection matrix is shown in FIG. 29.

The use of a gantry positioning apparatus to increase the field-of-view of an area detector, as described herein, possesses certain advantages over other techniques for improving the field-of-view in radiation imaging systems. For instance, by translating the entire gantry to move the detector closer to the object, the field-of-view is increased without decreasing the interior diameter of the gantry, and without having to increase the divergence of the x-ray cone beam, and thus the heel effect of the beam. Also, the present method of increasing the field-of-view is easily and quickly implemented, and does not require the expense of adding multiple detectors, or the complexity of moving the source to multiple positions to simulate a wide field-of-view. The present method also requires little or no additional time for data collection, and is particularly useful for applications in which imaging must be performed quickly and more safely, such as contrast injected rotational angioplasty.

The x-ray imaging systems and methods described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques. This invention could be used for acquiring multi-planar x-ray images in a quasi-simultaneous manner, such as described in commonly-owned U.S. patent application Ser. No. 10/389,268, filed on Mar. 13, 2003, the entire teachings of which are incorporated herein by reference.

The detector arrays of the present invention include two-dimensional flat panel solid-state detector arrays. It will be understood, however, that various detectors and detector arrays can be used in this invention, including any detector configurations used in typical diagnostic fan-beam or cone-beam imaging systems, such as C-arm fluoroscopes, or single-sliced or multi-sliced CT scanners, or mobile and fixed-room floroscopy devices which utilize image intensifier technology. A preferred detector is a two-dimensional thin-film transistor x-ray detector using scintillator amorphous-silicon technology.

In yet another aspect, the O-shaped gantry can include a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, the entire teachings of which are incorporated herein by reference.

In certain embodiments of the invention, such as where the gantry positioning apparatus translates and/or rotates the gantry to obtain images at multiple detector positions, the scanning system can be programmed to reproject data acquired at multiple detector positions onto a single virtual equilinear or equiangular detector array, such as described in co-pending U.S. application entitled "Apparatus and Method for Reconstruction of Volumetric Images in a Divergent Scanning Computed Tomography System," filed on even date herewith, the entire teachings of which are incorporated herein by reference.

Although the embodiments shown here include a five degree-of-freedom gantry positioning apparatus, it will be understood that various other embodiments of the invention exist where the gantry positioning apparatus is capable of translational or tilting movement in certain directions, but not in others.

While this invention has been particularly shown and described with references to preferred embodiments thereof, it will be understood by those skilled in the art that various changes in form and details may be made therein without departing from the scope of the invention encompassed by the appended claims. For instance, although the particular embodiments shown and described herein relate in general to x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

What is claimed is:

1. An imaging apparatus, comprising:
a gantry having a radiation source and a detector operable to obtain images of an object positioned inside the gantry;
a support structure;
a gantry positioning apparatus that secures the gantry to the support structure in a cantilevered manner; and
a processor which receives imaging data from the detector obtained at multiple gantry positions, and combines the data to extend the field of view of the imaging system;
wherein the gantry positioning apparatus comprises:
a first linear positioner for translating the gantry in a first direction relative to the support structure;
a second linear positioner for translating the gantry in a second direction relative to the support structure, the second direction being orthogonal to the first direction;
a third linear positioner for translating the gantry in a third direction relative to the support structure, the third direction being orthogonal to the first and second directions;
a first rotary positioner for rotating the gantry about a first axis relative to the support structure; and
a second rotary positioner for rotating the gantry about a second axis relative to the support structure.

2. The imaging apparatus of claim 1, further comprising:
a control system for controlling the translational and rotational movements of the gantry.

3. The imaging apparatus of claim 2, wherein the control system actuates the gantry positioning apparatus to move the gantry to a user-defined position and orientation.

4. The imaging apparatus of claim 2, wherein the control system actuates the gantry positioning apparatus to a position and orientation based upon stored positioning data.

5. The imaging apparatus of claim 2, further comprising a position feedback mechanism for determining the position of the gantry relative to the support structure.

6. The imaging apparatus of claim 1, wherein the source comprises an x-ray source.

7. The imaging apparatus of claim 6, wherein the x-ray source and detector are rotatable around the interior of the gantry to obtain object images at various projection angles.

8. The imaging apparatus of claim 7, wherein the x-ray source and detector are operable to obtain two-dimensional x-ray images of an object.

9. The imaging apparatus of claim 7, wherein the x-ray source and detector are operable to obtain three-dimensional computerized tomographic object images.

10. The imaging apparatus of claim 1, wherein the support structure comprises at least one of a wall, a floor, and a ceiling.

11. The imaging apparatus of claim 1, wherein the support structure comprises a cart.

12. The imaging apparatus of claim 1, wherein the support structure comprises a table for supporting an object to be imaged.

13. The imaging apparatus of claim 1, wherein the support structure is mobile.

14. The imaging apparatus of claim 1, further comprising a bracket for mounting the linear and rotary positioners.

\* \* \* \* \*